US005624805A

United States Patent [19]
Spencer et al.

[11] Patent Number: 5,624,805
[45] Date of Patent: Apr. 29, 1997

[54] USES FOR ANTIBODIES WHICH BIND TO HUMAN SOMATOMEDIN CARRIER PROTEIN SUBUNITS

[75] Inventors: Emerald M. Spencer, San Francisco; Carol Talkington-Verser, San Rafael, both of Calif.

[73] Assignee: Celtrix Pharmaceuticals, Inc., Santa Clara, Calif.

[21] Appl. No.: 440,228

[22] Filed: May 12, 1995

Related U.S. Application Data

[62] Division of Ser. No. 320,123, Oct. 7, 1994, which is a continuation of Ser. No. 43,039, Apr. 5, 1993, abandoned, which is a division of Ser. No. 763,481, Sep. 20, 1991, Pat. No. 5,200,509, which is a continuation of Ser. No. 290,250, Dec. 22, 1988, abandoned, and a continuation-in-part of Ser. No. 34,885, Apr. 6, 1987, abandoned, and a continuation-in-part of Ser. No. 170,022, Mar. 31, 1988, abandoned.

[51] Int. Cl.$^6$ .......... G01N 33/53; G01N 33/566; C07K 1/00
[52] U.S. Cl. .......... 435/7.1; 436/501; 530/395; 530/412
[58] Field of Search .......... 435/7.1; 530/395, 530/399, 412; 436/501

[56] References Cited

U.S. PATENT DOCUMENTS

| | | |
|---|---|---|
| 4,394,443 | 7/1983 | Weissman et al. . |
| 4,642,120 | 2/1987 | Nevo et al. . |
| 4,703,004 | 10/1987 | Hopp et al. . |
| 4,727,028 | 2/1988 | Santerre et al. . |
| 4,738,921 | 4/1988 | Belagaje et al. . |
| 4,861,757 | 8/1989 | Antoniades et al. . |
| 4,885,163 | 12/1989 | Shaar et al. . |
| 5,084,384 | 1/1992 | Wong et al. . |
| 5,104,796 | 4/1992 | Keith et al. . |
| 5,200,509 | 4/1993 | Spencer et al. . |
| 5,258,287 | 11/1993 | Baxter et al. . |
| 5,328,891 | 7/1994 | Baxter et al. . |

OTHER PUBLICATIONS

Chatelain, P.G. et al. J. Clin. Endocrinol. Metab. 56(2):376–383 (1983).
Clemmons, D.R. et al. J. Clin. Endocrinol. Metab. 56(2):384–389 (1983).
Scott, C.D. et al. Endocrinology 116(3):1094–1101 (1985).
Romanus, J.A. et al. Endocrinology 118(5): 1743–1758 (1986).
Abstract of Brewer et al., "Cloning, characterization, and expression of a human insulin–like growth factor binding protein" *Biochem. Biophys. Res. Comm.* (1988) 152:1289–1297.
Abstract of Brinkman et al., "Isolation and characterization of a complementary DNA encoding the low molecular weight insulin–like growth factor binding protein (IBP–1)" *EMBO J.* (1988) 7:2417–2424.
Abstract of Internatioal (PCT) Patent Publication No. WO 88/09818 (Dec. 15, 1988).

Morris et al., "Structure of somatomedin–binding protein: Alkaline pH–induced dissociation of an acid–stable, 60,000 molecular weight complex into smaller components" *Endocrinol.* (1982) 111:801–805.
Abstract of Furlanetto et al., "The somatomedin C binding protein: Evidence for a heterologous subunit structure" *J. Clin. Endocrinol. Metab.* (1980) 51:12–19.
Zapf et al., "Isolation and $NH_2$–terminal amino acid sequences of rat serum carrier proteins for insulin–like growth factors" *Biochem. Biophys. Res. Comm.* (1988) 156:1187–1194.
Abstract of International (PCT) Patent Publication No. WO 89/09792 (Oct. 19, 1989).
Abstract of International (PCT) Patent Publication No. WO 89/08666 (Sep. 21, 1989).
Smith, G.L., "Review–Somatomedin carrier proteins" *Mol. Cell. Endocrinol.* (1984) 34:83–89.
Drop et al., "Immunoassay of a somatomedin–binding protein from human amniotic fluid: Levels in fetal, neonatal, and adult sera" *J. Clin. Endocrinol. Metab.* (1984) 59:908–915.
Gourmelen et al., "Serum levels of insulin–like growth factor (IGF) and IGF binding protein in constitutionally tall children and adolescents" *J. Clin. Endocrinol. Metab.* (1984) 59:1197–1203.
Wood et al., "Cloning and expression of the growth hormone–dependent insulin–like growth factor–binding protein" *Mol. Endocrinol.* (1988) 2:1176–1185.
Baxter et al., "Growth hormone–dependent insulin–like growth factor (IGF) binding protein from human plasma differs from other human IGF binding proteins" *Biochem. Biophys. Res. Comm.* (1985) 139:1256–1261.

(List continued on next page.)

Primary Examiner—Christopher L. Chin
Assistant Examiner—Scott F. Welch
Attorney, Agent, or Firm—Morrison & Foerster LLP

[57] ABSTRACT

This invention relates to polypeptides that are human somatomedin carrier protein subunits and to processes for producing them. The carrier protein subunits bind to human somatomedin-like polypeptides, also known as insulin-like growth factors. The process involves preparation from a human serum fraction, Cohn IV-1, by a molecule of various chromatographic steps.

This invention also relates to DNA molecules encoding human somatomedin carrier protein-like polypeptides, recombinant DNA molecules, hosts, processes for producing carrier protein-like polypeptides, human somatomedin carrier protein-like polypeptides produced using those molecules, hosts and processes. The invention relates to DNA molecules and their expression in appropriate hosts. The recombinant DNA molecules contain DNA molecules that code for polypeptides which have a biological activity of the human carrier protein or a human carrier protein subunit capable of binding somatomedins. The DNA molecules, recombinant DNA molecules, hosts, and processes of this invention may be used in the production of polypeptides useful in a variety of therapeutic, diagnostic, and other useful applications.

2 Claims, 11 Drawing Sheets

OTHER PUBLICATIONS

Baxter et al., "Radioimmunoassay of growth hormone-dependent insulinlike growth factor binding protein in human plasma" *J. Clin. Invest.* (1986) 78:1504–1512.

Martin et al., "Insulin–like growth factor–binding protein from human plasma purification and characterization" *J. Biol. Chem.* (1986) 261:8754–8760.

Scheiwiller et al., "Growth restoration of insulin–deficient diabetic rats by recombinant human insulin–like growth factor I" *Nature* (1986) 323:169–171.

Koistinen et al., "Placental protein 12 is a decidual protein that binds somatomedin and has an identical N–terminal amino acid sequence with somatomedin–binding protein from human amniotic fluid" *Endocrinol.* (1986) 118:1375–1378.

Póvoa et al., "The somatomedin–binding protein isolated from a human hepatoma cell line is identical to the human amniotic fluid somatomedin–binding protein" *Biochem. Biophys. Res. Comm.* (1985) 128:1071–1078.

Schmid et al., "Intact but not truncated insulin–like growth factor binding protein-3 (IGFBP-3) blocks IGF I–induced stimulation of osteoblasts: Control of IGF signalling to bone cells by IGFBP-3–specific proteolysis?" *Biochem. Biophys. Res. Comm.* (1991) 179:579–585.

Yee et al., "Insulin–like growth factor binding protein 1 expression inhibits insulin–like growth factor I action in MCF–7 breast cancer cells" *Cell Growth & Differentiation* (1994) 5:73–77.

Sommer et al., "Molecular genetics and actions of recombinant insulin–like growth factor binding protein-3" *Modern Concepts of Insulin–Like Growth Factors*(1991) Spencer, E.M., ed., Elsevier Science Publishing Co., Inc. New York, pp. 715–728.

Sommer et al., "Properties of glycoslyated and non–glycoslyated human recombinant IGF binding protein-3 (IGFBP-3)" *Growth Regulation* (1993) 3:46–49.

Kalu, "The ovariectomized rat model of postmenopausal bone loss" *Bone and Mineral* (1991) 15:175–192.

Frost et al., "On the rat model of human osteopenias and osteoporoses" *Bone and Mineral* (1992) 18:227–236.

Spencer et al., "Somatomedins: Do they play a pivotal role in wound healing?" *Growth Factors and Other Aspects of Wound Healing: Biological and Clinical Implications* (1988) Alan R. Liss, Inc., pp. 103–116.

Steenfos et al., "Growth hormone stimulates granulation tissue formation and insulin–like growth factor–I gene expression in wound chambers in the rat" *J. Endocrinol.* (1992) 132:293–298.

Lawrence et al., "The reversal of an Adiramycin® induced healing impairment with chemoattractants and growth factors" *Ann. Surg.* (1986) 203:142–147.

Grotendorst et al., "Stimulation of granulation tissue formation by platelet–derived growth factor in normal and diabetic rats" *J. Clin. Invest.* (1985) 76:2323–2329.

Goodson III et al., "Development of a new miniature method for the study of wound healing in human subjects" *J. Surg. Res.* (1982) 33:394–401.

Bentley et al., "Peptides from live yeast cell derivative stimulate wound healing" *Arch. Surg.* (1990) 125:641–646.

Martin et al., "Antibody against acid–stable insulin–like growth factor binding protein detects 150,000 mol wt growth hormone–dependent complex in human plasma" *J. Clin. Endocrinol. Metabol.* (1985) 61:799–801.

Spencer et al., "Isolation of the human plasma carrier protein for somatomedin" *Abstracts, 7th International Congress of Endocrinology* (1984) p. 1278 (Abstract 2036).

Baxter et al., "Purification and radioimmunoassay of insulin––like growth factor binding protein from human plasma" *The Endocrine Society, 67th Annual Meeting* (Jun. 19–21, 1985) p. 201.

Grant et al., "Separation of the insulin–like growth factor binding proteins in human serum and charaterization of the acid stable component of the 150K species" *The Endocrine Society, 68th Annual Meeting* (Jun. 25–27, 1986) p. 83.

Gelato et al., "Heterogeneity of insulin–like growth factor (IGF) binding protein species derived from the $M_r$=150 K IGF–binding protein complex" *The Endocrine Society, 68th Annual Meeting* (Jun. 25–27, 1986) p. 83.

Kuffer et al., "Partial purification of a specific inhibitor of the insulin–like growth factors by reversed–phase high–performance liquid chromatography" *J. Chromatography* (1984) 336:87–92.

Knauer et al., "Purification and characterization of multiplication–stimulating activity (MSA) carrier protein" *J. Supramol. Struct. Cell. Biochem.* (1981) 15:177–191.

Enberg, "Purification of a high molecular weight somatomedin binding protein from human plasma" *Biochem. Biophys. Res. Comm.* (1986) 135:178–182.

Sofer et al., "Designing an optimal chromatographic purification scheme for proteins" *Biotechniques* (Nov./Dec. 1983) pp. 198–203.

Baxter et al., "Binding proteins for insulin–like growth factors in adult rat serum comparison with other human and rat binding proteins" *Biochem. Biophys. Res. Comm.* (1987) 147:408–415.

Romanus et al., "Insulin–like growth factor carrier proteins in neonatal and adult rat serum are immunologically different. Demonstration using a new radio immunoassay for the carrier protein from BRL–3A rat liver cells" *Endocrinol.* (1986) 118:1743–1758.

Lyons et al., "Characterization of multiplication–stimulating activity (MSA) carrier protein" *Mol. Cell. Endocrinol.* (1986) 45:263–270.

Póvoa et al., "Isolation and characterization of a somatomedin–binding protein from mid–term human amniotic fluid" *Eur. J. Biochem.* (1984) 144:199–204.

Wilkins et al., "Affinity–labeled plasma somatomedin–C–insulin–like growth factor I binding proteins. Evidence of growth hormone dependence and subunit structure" *J. Clin. Invest.* (1985) 75:1350–1358.

Holly et al., "The role of growth hormone in diabetes mellitus" *J. Endocrinol.* (1988) 118:353–364.

Zick et al., "Insulin–like growth factor I receptors in retinal rod outer segments" *J. Biol. Chem.* (1987) 262:10259–10264.

Schalch et al., "Effects of human growth hormone administration on serum somatomedins, somatomedin carrier proteins, and growth rates in children with growth hormone deficiency" *J. Clin. Endocrinol. & Metab.* (1982) 55:49–55.

Johansen et al., "Serum bone Gla–protein as a marker of bone growth in children and adolescents: Correlation with age, height, serum insulin–like growth factor I, and serum testosterone" *J. Clin. Endocrinol. & Metab.* (1988) 67:273–278.

Hossenlopp et al., "Analysis of serum insulin–like growth factor binding proteins using western blotting: Use of the method for titration of the binding proteins and competitive binding studies" *Anal. Biochem.* (1986) 154:138–143.

Binoux et al., "Somatomedin (insulin–like growth factors-)–binding proteins. Molecular forms and regulation" *Horm. Res.* (1986) 24:141–151.

Spadoni et al., "Measurement of insulin–like growth factor II in human serum by an homologous radioreceptor assay" *Abstracts, 7th International Congress of Endocrinology* (1984) p. 1278 (Abstract No. 2035).

Elgin et al., "Insulin–like growth factor (IGF) binding protein enhances the biologic response to IGF–1" *Proc. Natl. Acad. Sci. USA* (1987) 34:3254–3258.

D'Ercole et al., "Somatomedin–C/insulin–like growth factor I–binding proteins in human amniotic fluid in fetal and postnatal blood: Evidence of immunological homology" *J. Clin. Endocrinol. & Metabol.* (1985) 61:612–617.

Moses et al., "Demonstration that a human hepatoma cell line produces a specific insulin–like growth factor carrier protein" *J. Clin. Endocrinol. & Metabol.* (1983) 56:1003–1008.

Creighton, "Evolutionary and genetic origins of protein sequences" *Protein: Structures and Molecular Principles* (1983) W. H. Freeman & Co., New York, pp. 93–98.

Mottola et al., "Purification and amino–terminal sequence of an insulin–like growth factor–binding protein secreted by rat liver BRL–3A cells" *J. Biol. Chem.* (1986) 261:11180–11188.

Bowie et al., "Deciphering the message in the protein sequences: Tolerance to amino acid substitutions" *Science* (1990) 247:1306–1310.

AMINO TERMINAL

```
    TI ------------------------------------------ TI
                  GLY                             PHE
                  or                              or
    GLY-ALA-SER-SER-ALA-GLY-LEU-GLY-PRO-VAL-VAL-ARG-CYS-GLU-PRO-
    (1)                             (10)

T6 ----------------------------------------
    CYS-ASP-ALA-ARG-ALA-LEU-ALA-GLN-CYS-ALA-PRO-PRO-ALA-VAL-
                  (20)                              (30)
    ------ T6
    CYS-ALA-GLU-LEU-VAL-ARG-GLU-PRO-GLY-CYS-GLY-CYS-
                                        (40)
```

T-7

GLU-PRO-GLY-CYS-GLY-CYS-CYS-LEU-( )-CYS-ALA-LEU-SER-GLU-GLY-

GLN-PRO-( )-GLY-ILE-TYR

T-1

```
              ALA
              or
GLY-LEU-CYS-VAL-GLY-ALA-SER-ALA-VAL-SER-ARG
```

T-10

GLY-GLN-PRO-SER-PRO-ALA-GLU-ALA-ARG-PRO-LEU-GLN-ALA-LEU-LEU-

LEU-GLN

FIG. 1

```
                GLY                                              PHE
                 or                                               or
GLY-ALA-SER-SER-ALA-GLY-LEU-GLY-PRO-VAL-VAL-ARG-CYS-GLU-PRO-
                              (10)

CYS-ASP-ALA-ARG-ALA-LEU-ALA-GLN-CYS-ALA-PRO-PRO-PRO-ALA-VAL-
        (20)                                              (30)
                                                     >......
                                                     GCT GTG

CYS-ALA-GLU-LEU-VAL-ARG-GLU-PRO-GLY-CYS-GLY-CYS-CYS-LEU-( )-
                                    (40)
.....................  48mer  .......................>
TGT GCT GAG CTG GTG AGG GAG CCA GGC TGT GGC TGC TGC CTG

CYS-ALA-LEU-SER-GLU-GLY-GLN-PRO-( )-GLY-ILE-TYR
              (50)
```

FIG. 2A

```
            MET GLY ALA SER SER ALA GLY LEU
    5'..ACC ATG GGC GCC AGC AGC GCA GGT CTG

GLY PRO VAL VAL ARG CYS GLU PRO CYS
        GGT CCT GTG GTG CGC TGC GAG CCT TGT

ASP ALA ARG ALA LEU ALA GLN CYS ALA
        GAC GCT CGC GCT CTG GCT CAG TGC GCA

PRO PRO PRO ALA VAL CYS ALA GLU LEU
        CCT CCA CCA GCT GTG TGT GCC GAG CTG

VAL ARG GLU PRO GLY CYS GLY CYS CYS
        GTG AGA GAG CCT GGT TGC GGT TGT TGT

LEU GLY CYS ALA   LEU SER GLU GLY GLN
        CTG GGC TGT GCA   CTG AGC GAA GGC CAG

PRO ASN GLY ILE TYR ...
        CCA AAC GGG ATC TAT TAA T .... 3'
```

FIG. 2B

```
                    (1)                                                      (36)
         GA ATT CGG TGG GCG CTG AGG ATC AGC CGC TTC CTG CCT GGA TTC

(81)
         CAC AGC TTC GCG CCG TGT ACT GTC GCC CCA TCC CTG CGC GCC CAG (126)
         CCT GCC AAG CAG CGT GCC CCG GTT GCA GGC GTC ATG CAG CGG GCG
                                                              M   Q   R   A
              (-10)                                                (1)

(171)
         CGA CCC ACG CTC TGG GCC GCT GCG CTG ACT CTG CTG GTG CTG CTC
          R   P   T   L   W   A   A   A   L   T   L   L   V   L   L
                                     (10)

(216)
         CGC GGG CCG CCG GTG GCG CGG GCT GGC GCG AGC TCG GCG GGC TTG
          R   G   P   P   V   A   R   A   G   A   S   S   A   G   L
             (20)                                        (30)

(261)
         GGT CCC GTG GTG CGC TGC GAG CCG TGC GAC GCG CGT GCA CTG GCC
          G   P   V   V   R   C   E   P   C   D   A   R   A   L   A
                                     (40)

(306)
         CAG TGC GCG CCT CCG CCC GCC GTG TGC GCG GAG CTG GTG CGC GAG
          Q   C   A   P   P   P   A   V   C   A   E   L   V   R   E
             (50)                                        (60)

(351)
         CCG GGC TGC GGC TGC TGC CTG ACG TGC GCA CTG AGC GAG GGC CAG
          P   G   C   G   C   C   L   T   C   A   L   S   E   G   Q
                                     (70)

(396)
         CCG TGC GGC ATC TAC ACC GAG CGC TGT GGC TCC GGC CTT CGC TGC
          P   C   G   I   Y   T   E   R   C   G   S   G   L   R   C
             (80)                                        (90)

(441)
         CAG CCG TCG CCC GAC GAG GCG CGA CCG CTG CAG GCG CTG CTG GAC
          Q   P   S   P   D   E   A   R   P   L   Q   A   L   L   D
                                    (100)
```

FIG. 4A

```
                                                              (930)
GGC TTC TGC TGG TGT GTG GAT AAG TAT GGG CAG CCT CTC CCA GGC
 G   F   C   W   C   V   D   K   Y   G   Q   P   L   P   G
   (260)                                  (270)

(981)
TAC ACC ACC AAG GGG AAG GAG GAC GTG CAC TGC TAC AGC ATG CAG
 Y   T   T   K   G   K   E   D   V   H   C   Y   S   M   Q
                        (280)

AGC AAG TAG
 S   K   *
   (290)
```

USES FOR ANTIBODIES WHICH BIND TO HUMAN SOMATOMEDIN CARRIER PROTEIN SUBUNITS

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant no. SSS-C(3) 1 R43 HD21323-01 ENG awarded by the National Institute of Child Health and Human Development, Department of Health and Human Services and grant no. 2R44 HD21323-02.

This application is a division of application Ser. No. 08/320,123 filed Oct. 7, 1994 which is a continuation of Ser. No. 08/043,039 filed Apr. 5, 1993, abandoned, which is a divisional of Ser. No. 07/763,481, filed Set. 20, 1991, now U.S. Pat. No. 5,200,509, which is a continuation of Ser. No. 07/290,250, filed Dec. 22, 1988, abandoned, and a CIP of Ser. No. 07/034,885, filed Apr. 6, 1987, abandoned, and a CIP of Ser. No. 07/170,022, filed Mar. 31, 1988, abandoned.

FIELD OF THE INVENTION

This invention relates to human somatomedin carrier protein subunits and to processes for producing them. More particularly, this invention relates to carrier protein subunits that bind to human somatomedin-like polypeptides, also known as insulin-like growth factors. In addition, this invention relates to essentially pure human somatomedin carrier protein subunits. This invention also relates to processes of preparing such carrier protein subunits from human plasma. The process involves preparation from a human serum fraction, Cohn IV-1, by a sequence of various chromatographic steps. The carrier protein subunits and methods of this invention may be used in a variety of therapeutic, diagnostic or other useful applications.

This invention also relates to DNA molecules encoding human somatomedin carrier protein-like polypeptides, recombinant DNA molecules, hosts transformed with such molecules, processes for producing human somatomedin carrier protein-like polypeptides, and human somatomedin carrier protein-like polypeptides produced using those molecules, hosts and processes. More particularly, the invention relates to DNA molecules and their expression in appropriate hosts. The recombinant DNA molecules contain DNA molecules that code for polypeptides which have a biological activity of the human carrier protein. As will be appreciated from the disclosure to follow, the DNA molecules, recombinant DNA molecules, hosts, and processes of this invention may be used in the production of polypeptides useful in a variety of therapeutic, diagnostic, and other useful applications.

BACKGROUND OF THE INVENTION

Somatomedins (also sometimes referred to as "SMs") are hormones having useful biological properties. SMs are polypeptides having a molecular weight of approximately 7,500 daltons. SMs (a) mediate the growth-promoting effects of growth hormone. (also sometimes referred to as "GH"), (b) have weak insulin-like activity (and for that reason are also called "insulin-like growth factors" or "IGFs"), (c) are mitogenic for a variety of skeletal and other tissues and (d) are transported in plasma bound to a large carrier protein. There are two SM compositions in humans. SM-C is a basic polypeptide and is sometimes referred to as SM-C. SM-C mediates the growth promoting actions of GH after birth. SM-A is a mixture primarily of a polypeptide known as IGF-II and variable amounts of a modified form of SM-C. Spencer, E. M., et al., "The Identity Of Human Insulin-like Growth Factors I and II With Somatomedins C and A With Rat SM I and II" in *Insulin-like Growth Factors/Somatomedins*; ed. Spencer, E. M. (Walter de Gruyter 1983). IGF-II is less GH dependent and may have a role in fetal growth.

SMs may be useful in vivo to stimulate bone formation (for example, in treatment of osteoporosis), wound healing, and the growth of animals and GH-deficient humans. Serum levels of SM-C are measured to diagnose acromegaly, pituitary gigantism, GH deficiency, and other growth related conditions. Spencer, E. M., "Somatomedins" in *Basic and Clinical Endocrinology*, ads. Greenspan F. S. and Forsham, P. H. (1986), p. 89, Appleton-Century-Crofts. SMs are also employed to stimulate in vitro the proliferation of a variety of cells in tissue culture and, therefore, are useful in the study of the regulation of normal and abnormal cell growth. SMs produced by certain breast and kidney cancer cells may stimulate the proliferation of both the cancer cells and the vascular and fibrous tissues required to support the growth of the cancer tissues. Spencer, E. M. et al., "Possible Auto-stimulation of Human Mammary Carcinoma Growth by Somatomedins," Annals of the New York Acad. Sci., 464, p. 448 (1986): Huff, K. K., et al., "Secretion of Insulin-like Growth Factor-I-related Protein by Human Breast Cancer Cells," Cancer Research 46, pp. 4613–4619 (1986). Blocking the action of SMs may be useful to control the growth of these cancers.

Human SMs appear to be transported and regulated in vivo by other proteins. Hintz, R. L. et al., "Demonstration of Specific Plasma Protein Binding Sites For Somatomedin," *J. Clin. Endocrinol. Metab.* 45, p. 988 (1977). These proteins appear to bind to the SMs and regulate the biological activity of the SMs in vivo. Gel filtration of human serum at neutral pH has shown that 95% of the immunoreactive SM-C activity, and probably IGF-II activity, elutes at about 150,000 to 160,000 daltons (150–160 kilodaltons or "kDa") with a minor amount in the range of 35–50 kDa. Only a very small amount of immunoreactive activity elutes at 7.5 kDa, where free SMs should appear. Smith, G. L., *Molecular and Cellular Endocrinology* 34, p. 83–89 (1984). This indicates that SMs are complexed with larger proteins in plasma.

At least two different classes of proteins or protein complexes in human plasma have been reported to bind SMs. Drop, S. L. et al., "Immunoassay Of A Somatomedin-binding Protein From Human Amniotic Fluid; Levels In Fetal, Neonatal, And Adult Sere," *J. Clin. Endocrinol. Metab.* 59, p. 908 (1984): Wilkins, J. R. et al., "Affinity-labeled Plasma Somatomedin-C+/Insulin-like Growth Factor I Binding Proteins," *J. Clin. Invest.* 75, p. 1350 (1985). This description refers to one class of those native proteins or protein complexes as the SM "Carrier Protein" for its function appears to be the transport of SMs. This term is not intended to indicate that the carrier protein is a single protein. There may be more than one carrier protein and it may be a protein complex. This description refers to the other class as the "Amniotic Fluid Binding Protein" or "AFBP." There may be more than one AFBP. It is also possible that additional classes of proteins or protein complexes that bind SMs will be discovered.

Carrier protein activity, like SM-C activity, is GH-dependent, being low in persons with GH deficiency and elevated in patients with GH-producing tumors, a condition known as acromegaly. White, R. M., et al., "The Growth Hormone Dependence Of Somatomedin-binding Protein In Human Serum." *J. Clin Endocrinol Metab.* 53, p. 49 (1981). The carrier protein displays biological properties indicative of potentially valuable uses. In vivo, when SMs bind to carrier protein, the half-life of the SMs is reported to increase from approximately one hour to up to about 24 hours depending on the animal species tested (Cohen, K. L. et al., "The Serum Half-life Of Somatomedin Activity: Evidence For Growth Hormone Dependence," *Acta Endocrinol.* 83, p. 243 (1976)), and the SMs are rendered inactive until released. Studies in other model systems suggest that impure preparations containing the carrier protein (a) abolish the metabolic action of the SMs on the perfused rat heart (Meuli C., et al., "NSILA-carrier Protein Abolishes The Action of Nonsuppressible Insulin-like Activity (NSILA-s) On Perfused Rat Heart," *Diabetologia* 14, p. 255 (1978)), (b) inhibit the mitogenic effect of the SMs on cells in culture (Knauer, D. J., *Proc. Natl. Acad. Sci. U.S.A.*, 77, pp. 7252–7256 (1980) and Kuffer, A. D., et al., "Partial Purification Of A Specific Inhibitor Of The Insulin-like Growth Factors By Reversed Phase High-performance Liquid Chromatography," J. of Chromatography, 336, pp. 87–92 (1984) and (c) block the insulin-like activity of SMs on rat adipose tissue (Zapf, J., et al., "Inhibition Of The Action Of Nonsuppressible Insulin-like Activity On Isolated Rat Cells By Binding To Its Carrier Protein," *J. Clin Invest.* 63, p. 1077 (1979). Partially pure preparations of the carrier protein have been used with radiolabeled SMs in research to conduct competitive binding assays for measuring SMs. Moses, A. C., et al., *Endocrinology* 104, p. 536 (1979).

Because of their valuable biological properties, there have been many efforts to isolate and characterize the carrier protein or the subunits of the carrier protein responsible for that activity. Prior to this invention, all attempts to isolate and characterize in pure for the carrier protein or its active subunits have failed. This is due in part to the low concentration of carrier protein in plasma. A successful purification procedure also had to solve the problems of loss of activity because of enzymatic digestion and instability of the carrier protein, especially to changes in pH: Purification of the carrier protein subunits is further complicated by the presence in plasma of the AFBP, which also binds to somatomedins.

The carrier protein is a glycoprotein. In serum at neutral pH, it is bound with SMs and the complex has a molecular weight of about 150–160 kDa when measured by gel filtration. The molecular weight of the carrier protein complex at neutral pH has also been determined by other methods to be about 125 kDa. Gel filtration chromatography of serum or plasma under acid conditions has been reported to separate bound SMs from the carrier protein and to give rise to a unit of the carrier protein that has a molecular weight of about 40–50 kDa. That unit also binds to somatomedins. Hintz, R. L., et al., "Demonstration Of Specific Plasma Protein Binding Sites For Somatomedin," *J. Clin. Endocrinol. Metab.* 45, p. 988 (1977). Since the 40–50 kDa acid-stable unit cannot be induced to reform the 150–160 kDa carrier protein complex, others have suggested that the carrier protein may also be composed in part of an acid-labile unit that does not itself bind to somatomedins. Moses, A. C., et al., *Endocrinology* 104, p. 536 (1979). Furlanetto reported treating serum with a 35–55% ammonium sulfate solution, isolating the precipitate, dissolving the precipitate in 0.05M Tris. pH 8.20 and chromatographing on DEAE Sephadex A-50 with Tris buffers. Furlanetto, R. W., "The Somatomedin C Binding Protein: Evidence For A Heterologous Subunit Structure," *J. Clin. Endocrinol Metab.* 51, p. 12 (1980). Furlanetto did not disclose any further purification. Rather, Furlanetto conducted experiments with various fractions to confirm his view that the somatomedin-C binding activity in serum is composed of at least two units, one has a Stokes' radius of 36 A° and binds SM-C (the so-called acid stable unit) and the other has Stokes' radius of 30–38 A° and does not bind-SM-C (the so-called acid labile unit)).

Wilkins identified, by affinity labeling, plasma proteins that complexed with SM-C. Wilkins, J. R., et al., "Affinity-labeled Plasma Somatomedin-C/Insulin-like Growth Factor I Binding Proteins," *J. Clin. Invest.*, 75, p. 1350 (1985). $^{125}$I-SM-C was covalently cross-linked to proteins that bound SM-C in whole plasma and in Sephadex G-200 fractions of plasma. Following sodium dodecylsulfate polyacrylamide gel electrophoresis and autoradiography, the AFBP was identified in addition to species of about 160, 110, 80, 50 and 25 kDa. Wilkins et al. hypothesized that the 160 kDa carrier protein complex consisted of 6 approximately 25 kDa (24–28 kDa) subunit complexes, each composed of the subunit plus SM-C. However, Wilkins et al., did not report isolation or purification of this 25 kDa subunit. Another worker proposed, but did not establish, a slightly larger subunit structure. Daughaday, W. H., et al., "Characterization Of Somatomedin Binding in Human Serum By Ultracentrifugation And Gel Filtration," *J. Clin. Endocrinol. Metab.* 55, p. 916 (1982).

Several workers have reported unsuccessful attempts to isolate the acid-stable 40–50 kDa carrier protein unit from human plasma. Draznin et al., reported a material containing only 1% SM binding activity and did not disclose whether this material originated from carrier protein or AFBP. Draznin, B., et al., in "Somatomedins and Growth." eds. G. Giordano et al. (Academic Press 1979) pp. 149–160. Fryklund et al., fractionated fresh frozen human plasma by polyethylene glycol precipitation, carboxymethyl-Sephadex chromatography, and gel filtration. Fryklund, L., et al., in *Hormones and Cell Culture*, eds G. H. Sato et al. (Cold Spring Harbor Laboratory 1979) pp. 49–59. Fryklund et al., proposed that the carrier protein consisted of 2 dissimilar chains of 35 and 45 kDa. Fryklund et al., disclosed that glycine was released by N-terminal molecule analysis, but did not identify from which chain it originated or whether both ended in glycine. The reported binding activity of the Fryklund et al. preparation was very low and purity was not reported. Fryklund et al. did not establish whether the carrier protein or the AFBP was present in their preparation. Morris et al., reported obtaining crude SM binding fractions by acetic acid extraction of human Cohn fraction IV, incubation with I-IGF-I and chromatography on Sephacryl S-200. Morris, D. H., et al., "Structure of Somatomedin-binding Protein: Alkaline pH-Induced Dissociation of an Acid-Stable, 60,000 Molecular Weight Complex Into Smaller Components," *Endocrinology* 111, pp. 801–805 (1982). Morris et al. described fractions containing bound radioactive SM-C with apparent molecular weights of 60,000 and 46,000. Morris et al. reported that exposing these fractions to pH 8.0 resulted in a shift of $^{125}$I-IGF-I binding activity from 60,000 and 46,000 daltons to fractions with complexes of 46,000 and 30,000. These fractions were not further purified. Martin et al. reported preparing a polyclonal antibody to the acid-stable unit. The latter was isolated by extracting human Cohn fraction IV with 2M acetic acid, 75 mM NaCl. After removal of SMs by adsorption to SP-Sephadex, the acid stable unit was obtained by IGF-II-Affinity Chromatography and used for immunization. Martin et al. disclosed that HPLC could further purify the acid stable unit. No data was supplied to establish the purity of their final product. Martin, J. L., et al. "Antibody Against Acid-Stable Insulin-Like Growth Factor Binding Protein Detects 150,000 Molecular Weight Hormone-Dependent Complex In Human Plasma." *J. Clin. Endocrinol. Metab.* 261, pp. 799–801 (1985). Kuffer et al. reported a partial purification of what he described as an inhibitor of insulin-like growth factors (SMs). Kuffer. A. D. et al., "Partial Purification of A Specific Inhibitor of the Insulin-Like Growth Factors By Reverse Phase High-Performance Liquid Chromatography," *J. of Chromatography*, 336, pp. 87–92 (1984). Kuffer et al. prepared SM inhibitors having a molecular weight of 16,000 to 18,000 from Cohn fraction IV-1 by ion exchange chromatography and sequential gel chromatography under acid conditions on Sephadex G-75 and Bio-Gel P-30 columns. After affinity chromatography and high performance liquid chromatography, Kuffer et al. obtained the "inhibitory activity" as two peaks of activity, corresponding "to a major, apparently homogeneous, protein peak and a minor heterologous peak." Kuffer et al. did not report isolation of the activity of either peak.

None of the above studies disclose a class of human carrier protein subunits capable of binding somatomedin-like polypeptides. In addition, none of these studies disclose any subunits of the carrier protein capable of binding SMs and purified to homogeneity. Purity is required to establish that the carrier protein has been isolated instead of the AFBP or a contaminant and to study biologic activity. An impure preparation may contain enzymes, causing the product to be unstable, and easily degraded or denatured. Impure preparations also cannot be used in animals and humans, because many impurities present in original serum or produced as a result of the purification procedures, are antigenic and could produce unwanted biologic effects. For example, human use in osteoporosis requires removal of all contaminants, which may be antigenic or have adverse biologic effects.

Other workers have isolated a different protein capable of binding SMs and obtained from mid-gestational amniotic fluid of humans, the amniotic fluid binding protein or "AFBP." The AFBP is not the carrier protein or a subunit of the carrier protein. Wilkins. J. R. et al., "Affinity-labeled Plasma Somatomedin-C/Insulin-like Growth Factor I Binding Proteins." *J. Clin. Invest.* 75, p. 1350 (1985). The AFBP (a) is smaller than the so-called acid-stable unit of the carrier protein, having a molecular weight in the range 32–40 kDa, (b) is not glycosylated, (c) differs from the carrier protein subunits of this invention in its reported N-terminal molecule (Povoa, G. et al., "Isolation And Characterization of A Somatomedin-binding Protein From Mid-term Human Amniotic Fluid," *Eur. J. Biochem.* 144, pp. 199–204 (1984) ), and (d) has different immunologic properties. Drop, S. L. S. et al., "Immunoassay of A Somatomedin-Binding Protein From Human Amniotic Fluid: Levels In Fetal, Neonatal and Adult Sere," *J. Clin. Endocrinol. Metab.* 59, p. 908 (1984); Martin, J. L. et al., Supra, *J. Clin. Endocrinol. Metab.* 61, pp. 799–801 (1985). Antisera to the AFBP do not cross-react with the 150 kDa carrier protein or its acid-stable unit. Drop et al. reported that the AFBP levels determined by radioimmunoassay (RIA) were found to decrease during infancy and childhood—the inverse of the carrier protein and also, unlike the carrier protein, to have a significant diurnal variation. Enberg also isolated the AFBP from adult human plasma by four chromatographic steps: CM-Affigel blue, hydroxylapatite, fast protein liquid chromatography gel permeation and high performance liquid chromatography ("HPLC") hydroxylapatite. Enberg, G., "Purification of A High Molecular Weight Somatomedin Binding Protein From Human Plasma," *Biochem, and Biophy. Res. Commun.*, 135, pp. 178–82 (1986). Enberg reported a "possible" N-terminal molecule, Ala-Pro-Trp-, demonstrating that the AFBP was isolated, not the 150 kDa carrier protein as Enberg erroneously concluded.

Proteins that bind SMs have also been identified in cell culture extracts (e.g., Adams, S. O., et al. *Endocrinology* 115, pp. 520–526 (1984)). Thus far, the carrier protein has not been isolated. Spencer first showed that primary cultures of liver cells produced a protein that complexes with SMs. Spencer, E. M, "The Use Of Cultured Rat Hepatocytes To Study The Synthesis Of Somatomedin And Its Binding Protein," *FEBS Letters*, 99, p. 157, (1979). Subsequently, several cell types, normal and abnormal, have been found to synthesize a protein that complexes with SMs. Cultured Buffalo rat liver tumor cells (BRL 3A) produce a 33 kDa SM binding protein that differs from the carrier protein by antibody reactivity, N-terminal amino acid molecule, and absence of glycosylation. Lyons R. M. et al., Characterization of Multiplication-Stimulatory Activity "MSA" Carrier Protein, "*Molecular and Cellular Endocrinol.* 45, pp. 263–70 (1986). Mottola. C. et al., *J. of Biol. Chem.*, 261, pp. 1180–88 (1986). Romanus et al. reported that antibodies to this binding protein cross-reacted with a protein present in fetal serum but not adult rat serum. Romanus, J. A. et al., "Insulin-like Growth Factor Carrier Proteins In Neonatal And Adult Rat Serum Are Immunologically Different: Demonstration Using A New Radioimmunoassay For The Carrier Protein From BRL-3A Rat Liver Cells," *Endocrinology*, 118, p. 1743 (1986). The BRL-3A binding protein may be the rodent equivalent of the AFBP, but the N-terminal molecule data show no similarity between the two molecules.

Many proteins and polypeptides have been produced by use of recombinant DNA techniques. There is no published report of production of carrier protein-like polypeptides in this manner. There are numerous obstacles to using the techniques of recombinant DNA technology to clone and express a carrier protein-like polypeptide gene. Obtaining a gene encoding a carrier protein-like polypeptide is difficult for a variety of reasons. Prior to the invention, the protein sequences of the carrier protein and the carrier protein subunits were unknown and, therefore. DNA molecules that, would code for the subunits were unknown. No human tissue source was established. Fibroblasts had been shown to produce small amounts of a large uncharacterized SM binding protein (Adams. S. O., et al. *Endocrinology* 115, pp. 520–526 (1984)). While liver is the major source of somatomedins, it had never been shown to produce the carrier protein. In addition, the liver is difficult to use to isolate mRNA, due to ribonucleases, the quantities of carrier protein in serum are very low. Thus, mRNA might be rare. The genome including a DNA molecule coding for the carrier protein may contain intervening sequences. For these and other reasons, many pitfalls faced the conventional approach to attempt to isolate a gene encoding a carrier protein-like polypeptide —namely, identifying a source of mRNA containing large amounts of the desired molecule, creating a library of cDNA from that mRNA, screening the library with oligonucleotide probes designed to hybridize with cDNA having the desired molecule, and isolating or assembling a gene from those cDNA molecules.

DISCLOSURE OF THE INVENTION

In this description, the following terms are employed:

Somatomedin-like—A polypeptide displaying the biological activities of one of the human SMs or insulin-like growth factors, including but not limited to SM-C, SM-A, IGF-I and IGF-II. That polypeptide may have amino acids in addition to those of native human SMs or it may not include all the amino acids of native human SMs.

Carrier Protein—A glycoprotein or complex of glycoproteins in human plasma, displaying the ability to regulate the biological activity of the human SMs in vivo by a process involving binding of the SM-like polypeptides, being growth hormone dependent, and exhibiting an apparent molecular weight of about 125,000–160,000 daltons in physiological pH conditions when complexed with SMs. The carrier protein may also be polymorphic. For example, cells of different individuals may produce carrier protein species which are physiologically similar, but structurally slightly different from the prototype.

Subunit—A polypeptide fragment, part, or component of a larger protein unit. The term subunit is not confined to its customary meaning of a discrete polypeptide chain bound by covalent or any other types of bonds to another discrete polypeptide chain.

Carrier Protein Subunits—A class of subunits of the carrier protein.

Polypeptide—A linear chain of amino acids connected by peptide bonds. A polypeptide may also contain one or more disulfide bonds between cystines of the same amino acid chain.

Carrier Protein-like Polypeptide—A polypeptide displaying a human somatomedin regulating biological activity of the carrier protein and being capable of binding somatomedin-like polypeptides. Preferably, a carrier protein-like polypeptide displays a somatomedin-C regulating activity of the carrier protein. A carrier protein-like polypeptide may be a carrier protein subunit capable of binding somatomedin-like polypeptides, if it possesses such somatomedin regulating activity. This polypeptide may include one or more amino acids in addition to those of the carrier protein or such carrier protein subunits. This polypeptide may not include all of the amino acids of the carrier protein or such carrier protein subunits because one or more amino acids have been deleted or because one or more amino acids have been substituted for others. Thus, a carrier protein-like polypeptide may have the amino acid sequence of the carrier protein or of a carrier protein subunit in which an amino acid residue has been added, deleted or substituted. A carrier protein-like polypeptide may have the natural glycosylation of the carrier protein, may lack the natural glycosylation of the carrier protein, or may have glycosylation different from the natural glycosylation of the carrier protein. Thus, a carrier protein-like polypeptide may be unaccompanied by the associated natural glycosylation of the carrier protein. This polypeptide preferably has a molecular weight of about 40,000–50,000 daltons or less, if measured in a form accompanied by natural glycosylation. This polypeptide more preferably has a molecular weight of about 30,000 daltons or less, if measured in that form.

Somatomedin-C ("SM-C" or "IGF-I")—The principle hormone regulating growth after birth. SM-C mediates the growth promoting action of GH and binds to the carrier protein.

Nucleotide—A monomeric unit of DNA or RNA consisting of m sugar moiety (pentose), a phosphate, and a heterocyclic base. The four DNA bases are adenine ("A"), quanine ("G"), cytosine ("C"), and thymine ("T"). The four RNA bases are A, G, C, and uracil ("U").

DNA Molecule—A molecule other than the entire human genome composed of a sequence of nucleotides connected one to the other by phosphodiester bonds between the 3' and 5' carbons of adjacent pentoses. A DNA molecule may be composed of an isolated sequence of nucleotides that are part of the human genome. A DNA molecule may be composed of a single DNA molecule (commonly called "single stranded DNA") or two DNA molecules composed of complementary nucleotides (commonly called "double stranded DNA").

Recombinant DNA Molecule—A DNA molecule having at least one nucleotide sequence resulting from Joining or adding together at least two DNA molecules.

Genome—The entire DNA of a cola or a virus. It includes the genes coding for the polypeptides of the organism, as well as operators, promoters and ribosome binding and other interaction sites.

Gone—A DNA molecule which encodes through its mRNA a sequence of amino acids of a specific polypeptide.

cDNA—A double-stranded DNA molecule produced from an RNA molecule by using that RNA as a template for RNA-directed synthesis of the first DNA strand followed by using that DNA strand as a template for DNA-directed synthesis of the second DNA strand.

Transcription—The process of producing mRNA from a gone.

Translation—The process of producing a polypeptide from mRNA.

Expression—The process of producing a polypeptide by transcription and translation.

Plasmid—A nonchromosomal double-stranded DNA molecule comprising an intact "replicon" such that the molecule is replicated in a host organism. When the plasmid is placed within a single celled organism, the characteristics of that organism may be changed as a result of the DNA of the plasmid. A cell transformed by a plasmid is called a "transformant."

Virus—DNA or RNA molecules in a protein envelope or coat capable of infecting a cell or organism.

Phage or Bacteriophage—Bacterial virus.

Vehicle or Vector—A plasmid, phage, mammalian virus, cosmid, or other DNA molecule which is able to be transformed into and to replicate in a host, having one or more sites at which such DNA molecules may be cut in a determinable fashion without loss of an essential biological function of the DNA, e.g., replication, production of coat proteins or loss of promoter or binding sites, and having a marker suitable for use in the identification of a transformed host, e.g., tetracycline resistance.

Cloning—A process of obtaining a population of organisms, cells or DNA molecules derived from one such organism, cell or DNA molecule.

Expression Control Sequence—A DNA sequence that controls and regulates expression of genes when operatively linked to those genes. They include the lac system, the trp system, the tac system, the trc system, major operator and promoter regions of phage λ, the T7 system, the control region of fd coat protein, the control sequences of SV-40, the actin system, the metallothionein system, the LTR (promoter-containing long terminal repeat of retroviruses) system, and other sequences known to control the expression of genes of prokaryotic or eukaryotic cells or organisms and their viruses or combinations thereof.

Host, Host Organism or Host Cell—A prokaryotic or eukaryotic cell or organism capable of being transformed by a vehicle or vector.

Carrier Protein Subunits

The invention solves the problems referred to by making available human carrier protein subunits capable of binding somatomedin-like polypeptides. The ability of the carrier protein subunits of the invention to bind somatomedin-like polypeptides has been demonstrated by binding those subunits in vitro to somatomedin-C at about physiological pH. This binding activity demonstrates that the carrier protein subunits of the invention will bind somatomedin-like polypeptides in vivo, and provide substantially the transport and regulatory activity of the native carrier protein. When this description refers to the capability of the carrier protein subunits to bind somatomedin-like polypeptides, it is referring to this ability to bind such polypeptides in vitro or in vivo. The carrier protein subunits have no substantial binding activity for insulin.

The carrier protein subunits of the invention each constitute a single polypeptide chain. The carrier protein subunits of the invention have an N-terminal amino acid molecule of the formula:

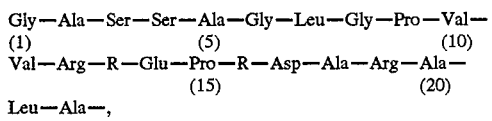

wherein R is cysteine or half-cystine. Half-cystine refers to an amino acid bound to another half-cystine amino acid in the same polypeptide chain by a disulfide bond. Because the carrier protein may be polymorphic, the amino acid molecule of the carrier protein subunits may also vary depending on the polymorphic character of the carrier protein. For example, the carrier protein subunits may contain a glycine ("Gly") residue in place of the alanine ("Ale") at position 5 from the N-terminal. Similarly, the Glu at position 14 from the N-terminal may sometimes be replaced in part by Phe.

The carrier protein subunits of the invention have a range of molecular weights. The molecular weights of the carrier protein subunits referred to in this description are those determined by SDS-PAGE gel electrophoresis against proteins of known weight conducted in the presence of a suitable reducing agent such as B-mercaptoethanol "BME." The known protein standards were 200,000 (myosin (H-chain)), 97.400 (phosphorylase b), 66,200 (bovine serum albumin) 43,000 (ovalbumin), 25,700 (α chymotrypsinogen), 18,400 (β-lactoglobulin and 14,300 (lysozyme). Carrier protein subunits having molecular weights of about 15,000, 21,000, 26,000 and 30,000 daltons have been isolated and identified. The carrier protein subunits may differ in molecular weight because they were present in the carrier protein as polypeptides of that size or because of enzymatic digestion or break-down from other causes. Whatever the source of these differences, the carrier protein subunits of the invention have a molecular weight of about 30,000 or less. The carrier protein subunits of the invention preferably have a molecular weight of about 15,000 to and including about 30,000 daltons.

The carrier protein subunits of the invention are glycoproteins, as shown by their positive reaction to the periodic acid Schiff reagent and ability to bind concanavalin A cross-linked to agarose (Con-A Sepharose, Pharmacia). Binding to Con-A Sepharose is specific for glycoproteins containing glucose and mannose residues. Specific residues include α-D-mannopyranosyl and α-D-glucopyranosyl residues. Therefore, the carrier protein subunits are substantially glycosylated.

The invention also provides essentially pure carrier protein subunits having SM binding activity. The carrier protein subunits of the invention are essentially free of other proteins, peptides, nucleotides, polysaccharides, lipids and salts. By virtue of the invention, it is possible to obtain those subunits in sufficient purity for use in human and animal therapeutic agents, as animal growth promotion agents, in human and other animal diagnostic reagents, and in human and other animal research applications.

The invention also provides therapeutic compositions comprising an effective amount of at least one carrier protein subunit capable of binding somatomedin-like polypeptides, or pharmacologically acceptable salts thereof, and a pharmacologically acceptable carrier. The carrier protein subunit of such therapeutic compositions may be at least one essentially pure carrier protein subunit. Compositions of carrier protein subunits of the invention have many therapeutic uses involving the important biological properties of SMs. Compositions comprising the human carrier protein subunits may be useful in treatment of diseases involving increased, unregulated SM-dependent growth. Thus, the ability of the carrier protein subunits of the invention to inactivate SMs by binding permits a new therapy of several conditions. In such therapies, it is apparent that an effective amount of the carrier protein subunit is an amount sufficiently in excess of the biologically active, unregulated SMs to block or inactivate the SM activity. For example, an effective amount of carrier protein subunit may be 10 or more times the amount of biologically active SMs on a molar basis. For example, some cancers have been shown to produce SMs: fibrosarcomas, chondrosarcomas and hepatoma cell lines. De Larco, J. E., et al., "A Human Fibrosarcoma Cell Line Producing Multiplication Stimulating Activity "MSA"-related Peptides," *Nature*, 272, pp. 356–358 (1978). Breast and renal cancers produce a SM which autostimulates the growth of the cancer. Spencer, E. M. et al., "Possible Auto-stimulation Of Human Mammary Carcinoma Growth By Somatomedins," Annals New York Academy Sciences, 464, pp. 448–449 (1986). Since endothelial cell and fibroblast proliferation are also stimulated by SMs, SMs produced by breast cancers can act also as a paracrine and stimulate the growth of the supporting stromal tissue critical to tumor survival. Bar, R. S., et al., "Receptors For Multiplication-stimulating Activity on Human Arterial and Venous Endothelial Cells, *J. Clin. Endocrinol. Metab.* 52, p. 814, (1981); Clemmons, D. R., et al., "Hormonal Control Of Immunoreactive Somatomedin Production By Cultured Human Fibroblasts." *J. Clin. Invest* 67, p. 10 (1981). By blocking the action of SMs, administering the human carrier protein subunit of the invention would be expected to reduce the rate of tumor growth and additionally render the malignant cells more sensitive to other drugs.

Carrier protein subunit therapy could also help prevent blindness secondary to diabetic proliferative retinopathy. Spencer and others have shown that SM-C seems to be one of the factors stimulating endothelial and fibroblast proliferation in diabetic retinopathy. Lorenzi, M., Spencer, E. M. et al., "Improved Diabetic Control, Growth Factors and Rapid Progression of Retinopathy," *New England Journal of Medicine*, 308, p. 160, (1983); Ashton, I. K., et al., "Plasma somatomedin in diabetics with retinopathy and joint contractures" in *Insulin-Like Growth Factors/Somatomedins.*, ed. Spencer, E. M. (Walter de Gruyter). The ability of the carrier protein subunit to block this adverse effect of SM-C (and possibly also IGF-II) could be a useful new therapy.

The carrier protein subunits of the invention are also useful to produce antibodies. The invention will enable pure carrier protein subunits to be used as the antigen to produce both polyclonal antibodies with high titers, high affinities or blocking properties, and monoclonal antibodies that are not now available. These antibodies could be used for immunoassays to make specific measurements, for blocking carrier protein activity, affinity chromatography and immunohisto-chemistry.

The carrier protein subunits can also be used to develop the first procedure to measure the free level of SMs in body fluids. This method would improve current methods that can only measure total SMs because the free level is really what determines their biological activity. The carrier protein subunit antibody would be used to separate the SM-carrier protein complex from the free SMs in fluids. The free SMs could then be measured by, for example, RIA.

This invention also provides a composition comprising at least one carrier protein subunit substantially complexed with at least one somatomedin-like polypeptide. Such a composition would have a variety of therapeutic applications. SMs possess biological activity which make them potentially useful in many therapeutic applications. However, to maintain the required steady level of SMs in plasma, multiple daily injections would have to be given because the half-life of SMs may be less than one hour in the free condition. This obstacle cannot be overcome by administering a larger dosage because (a) SMs are potent mitogens for subcutaneous, muscular, and vascular tissues (fibroblasts, endothelial cells, muscle cells, adipocytes, and endothelial cells) and could produce local tissue proliferation, (b) large amounts of free SMs would cause hypoglycemia, and (c) the excessive amount of SMs required to maintain a steady plasma level would not be cost effective.

SM could be delivered to target tissues in a safe, effective physiologic manner and their half-life significantly prolonged by complexing them to the carrier protein subunits of the invention. The SM in a SM-carrier protein subunit complex would not be mitogenic at injection sites or hypoglycemic. This complex could be formulated to provide controlled, long-term absorption. After transport to target tissues, dissociation would release SM. Thus, therapy would mimic the physiologic delivery system. Successful therapeutic and animal husbandry use of SM-C, IGF-II and other somatomedin-like polypeptides are permitted by a composition of at least one human somatomedin-like polypeptide and at least one carrier protein subunit. Compositions comprising one or more carrier protein subunit and one or more SMs would also be useful for treatment of diseases such as postmenopausal osteoporosis, other forms of osteoporosis, and human GH deficiency, as well as for healing wounds and increasing animal growth. Such composition would be used to deliver SM to bony tissues and stimulate the growth of bone. Dissociation of the SM from the carrier protein subunit-SM complex should stimulate osteoblasts to increase bone formation in postmenopausal osteoporosis, invade the porous matrix of a prosthetic Joint thereby stabilizing the prosthesis, and to promote healing of un-united fractures.

Therapeutic compositions comprising an effective amount of at least one carrier protein subunit capable of binding somatomedin-like polypeptides, or pharmacologically acceptable salts thereof, and a pharmacologically acceptable carrier and therapeutic processes using such compositions may also be useful in treating injuries or diseases in which the natural healing mechanism or response involves the presence of regulated levels of biologically active somatomedins. For example, such compositions may be useful in wound healing, where the natural physiological response involves the presence of endogenous SMs at the site of the wound. An effective amount of carrier protein subunit is an amount sufficient to prolong the half-life of the endogenous biologically active somatomedins.

Compositions of at least one carrier protein subunit and SM-C can be used as an effective biodegradable growth-enhancer in animal husbandry. Currently antibiotics and steroids ere commercially important animal growth promoters. Because there are serious health concerns with both classes, new agents are being sought, especially biodegradable ones. GH has been investigated. However, the SM-C-carrier protein subunit complex may be much more effective, because SM-C is the direct mediator of the growth promoting effect of GH. SM-C is neither diabetogenic nor lipolytic. For the same reasons applied to postmenopausal osteoporosis, the SM-C would have to be administered in composition with the carrier protein subunit.

For all of these reasons, there have been many attempts to determine the protein structure needed. For carrier protein-like activity. None have identified and isolated the carrier protein subunits of this invention or isolated them in pure form.

Another aspect of the invention is a process for producing the human carrier protein subunits from human plasma comprising (a) chromatographing the portions of Cohn fraction IV-1 that are soluble in an aqueous solution of pH of about 4.5 to 7.5 on a sulfopropyl derivative of a cross-linked dextran adsorbent by sequentially eluting with aqueous solutions of increasing pH; (b) chromatographing an acidic solution of pH less than about 4.0 of the fractions from step (a) that contain somatomedin binding activity on the same adsorbent as step (a) and collecting the pass-through fraction, or chromatographing the fractions from step (a) on a phenyl derivative of agarose by adsorption from a neutral solution of about 10% ammonium sulfate and eluting with about 0.5M sodium thiocyanate solution at about neutral phi (c) chromatographing the fraction from step (b) containing somatomedin binding activity by gel filtration and eluting with an acidic aqueous solution; (d) chromatographing the fraction from step (c) containing somatomedin binding activity on a solid support cross-linked to substantially pure somatomedin-C by adsorbing at about neutral pH and eluting with an acidic aqueous solution; and (e) chromatographing the fraction from step (d) containing somatomedin binding activity by reverse phase high performance liquid chromatography.

Recombinant DNA And Carrier Protein-Like Polypeptides

The present invention also involves locating, identifying, and isolating DNA molecules that code for carrier protein-like polypeptides, recombinant DNA molecules, vectors, hosts and methods for the use of those molecules, vectors and hosts in the production of carrier protein-like polypeptides, that is, polypeptides displaying a somatomedin regulating activity of a carrier protein and being capable of binding somatomedin-like polypeptides. By virtue of this invention, it is possible to obtain carrier protein-like polypeptides for use in therapeutic and diagnostic compositions and methods. This invention allows the production of these polypeptides in amounts and by methods not available previously. This invention also involves producing these polypeptides essentially, and more preferably completely, free of other polypeptides naturally present in human plasma.

As will be appreciated from the disclosure, the DNA molecules and recombinant DNA molecules of the invention contain genes that are capable of directing the expression, in an appropriate host, of carrier protein-like polypeptides. Replication of these DNA molecules and recombinant DNA molecules in appropriate hosts also permits the production in large quantities of genes coding for these polypeptides. The molecular structure and properties of these polypeptides and genes may thus be readily determined. The polypeptides and molecules are useful, either as produced in the host or after appropriate modification, in compositions and methods for improving the production of these products themselves and for use in therapeutic and diagnostic compositions and methods.

A basic aspect of this invention is the provision of a DNA molecule comprising a gene which codes for a carrier protein-like polypeptide, namely one displaying a somatomedin regulating activity of the carrier protein and being capable of binding somatomedin-like polypeptides. Such a DNA molecule has been isolated in the sense that it is not the entire human genome. Such a DNA molecule is preferably free of introns. Such a DNA molecule is also preferably essentially free of genes which code for any other polypeptide coded for by the human genome. Preferably, such a gene codes for a polypeptide having a molecular weight of about 40,000–50,000 daltons or less, if molecular weight is measured in a form accompanied by natural glycosylation. Such a gene may code for a polypeptide displaying a somatomedin regulating activity of the carrier protein, and more preferably, a somatomedin-C regulating activity of the carrier protein. Such a gene may also code for a carrier protein-like polypeptide that is a carrier protein subunit capable of binding somatomedin-like polypeptides, and more preferably a carrier protein subunit capable of binding somatomedin-C.

The invention also provides a process for obtaining a DNA molecule, comprising preparing cDNA molecules from mRNA found in cells or tissues that produce the carrier protein, determining which of the cDNA molecules hybridize to one or more labelled polynucleotide probes based on the DNA sequence of FIG. 4, analyzing the cDNA molecules that hybridized, and obtaining a DNA molecule having a gone which codes for a carrier protein-like polypeptide. In that process, a DNA molecule having the gone may be obtained by ligating one or more cDNA molecules that hybridized with other cDNA molecules, synthetic DNA molecules, or recombinant DNA molecules. The cDNA molecule which hybridizes to said probe may be a cDNA molecule selected from the group consisting of a human liver gene library, a human fibroblast gone library, a human placenta library, and a human epithelial library. In that process, the labelled polynucleotide probe may have the DNA sequence shown in FIG. 2a. The invention also includes a DNA molecule made by that process, and a DNA molecule which encodes a carrier protein-like polypeptide coded for by a DNA molecule obtainable by that process.

The invention also provides an oligonucleotide probe having all or a portion of the DNA sequence of any one of the DNA molecules LCP, LCP 0.70, LCP 0.77, LCP 2.3, LCP 2.5, FCP 1.8 and FCP 2.5, which selectively hybridizes to a DNA molecule encoding a carrier protein-like polypeptide.

In addition, a DNA molecule of the invention may be selected from the group consisting of the DNA molecule LCP 0.70, LCP 0.77, LCP 2.3, LCP 2.5, FCP 1.8 and FCP 2.5, DNA molecules which hybridize to any of the DNA molecules LCP 0.70, LCP 0.77, LCP 2.3, LCP 2.5, FCP 1.8 and FCP 2.5, and which code for a carrier protein-like polypeptide, and DNA molecules which code for a polypeptide coded for by any of the foregoing DNA molecules. A preferred DNA molecule comprises a DNA molecule which is the carrier protein-related portion of LCP 2.3. Another recombinant DNA molecule comprises a DNA molecule which is the carrier protein-related portion of LCP 2.3, and DNA molecules which code for a polypeptide coded for by said portions of LCP 2.3.

Furthermore, a DNA molecule of the invention may comprise a gene which codes for a polypeptide having the sequence of amino acids −1 to 290 of FIG. 4, amino acids 1 to 290 of FIG. 4, or amino acids 27 to 290 of FIG. 4. A DNA molecule may also comprise a gene which codes for a polypeptide having the sequence of amino acids 27 to 290 of FIG. 4 and having a methionine residue preceding amino acid 27.

A DNA molecule may also comprise a gene which codes for a polypeptide having the sequence of amino acids 27 to 290 and having a sequence of amino acid residues preceding amino acid 27 that constitute a secretion, signal or other precursor sequence recognized by a host.

These DNA molecules may be used to construct a recombinant DNA molecule in which such DNA molecules are operatively linked to an expression control sequence. Preferably, such a recombinant DNA molecule constitutes a vector or vehicle. The invention provides a method for producing a vector comprising introducing into a vector such a DNA molecule. That method may comprise the additional step of introducing into said vector an expression control sequence, so as to control and to regulate the expression of that DNA molecule. The expression control sequence may be a lac system, a trp system, a tac system, a trc system, a T7 system, major operator and promoter regions of phage λ, the control region of fd coat protein, the control sequences of SV-40, the actin system, the metallothionein system, the LTR (promoter containing long terminal repeat of retrovirus) system, and other sequences which control the expression of genes or prokaryotic or eukaryotic cells and their viruses and combinations thereof.

The recombinant DNA molecules and vectors of this invention permit the production of carrier protein-like polypeptides in hosts. The invention also includes a host transformed with at least one of those recombinant DNA molecules or vectors. A transformed host may be strains of *E. coli*, Pseudomonas, *Bacillus subtilis*, *Bacillus stearothermophilus*, other bacteria, yeast, fungi, animal, insect or plant hosts and human tissue cells.

The invention provides a method for producing a carrier protein-like polypeptide, comprising the steps of transforming an appropriate host with such a recombinant DNA molecule or vector, and culturing said host to make such a polypeptide. Preferably, the method includes the additional step of collecting said polypeptide. In this method, the host may be strains of *E. coli*, Pseudomonas, *Bacillus subtilis*, *Bacillus stearothermophilus*, other bacteria, yeasts, fungi, animal, insect or plant hosts, and human tissue cells. The method for producing such a polypeptide may also comprise the steps of culturing a host transformed by such a recombinant DNA molecule or vector.

The invention also provides a polypeptide that is coded for on expression by a recombinant DNA molecule or vector described above.

The invention also provides an essentially pure carrier protein-like polypeptide other than a carrier protein subunit capable of binding somatomedin-like polypeptides. Such an essentially pure polypeptide is preferably essentially free of substances naturally present in human serum. Such a polypeptide may be a mature carrier protein-like polypeptide. Such a mature polypeptide is one in which the amino acid residues constituting a secretion, signal or other precursor sequence are deleted.

The invention provides an essentially pure polypeptide having the sequence of amino acids −1 to 290 of FIG. 4.

It also provides an essentially pure polypeptide having the sequence of amino acids 1 to 290 of FIG. 4. The invention includes a polypeptide having the sequence of amino acids 27 to 290 and having a methionine residue preceding amino acid 27. It further provides an essentially pure polypeptide having the sequence of amino acids 27 to 290 of FIG. 4.

The invention includes polypeptides having the sequence 27 to 290 in which one or more amino acid residues may have been added, deleted or substituted, so long as the polypeptide remains a carrier protein-like polypeptide.

The invention includes a polypeptide having the sequence of amino acids −1 to 290 of FIG. 4, and polypeptides that have a portion of that sequence and have a somatomedin regulating activity of the carrier protein and are capable of binding somatomedin-like polypeptides.

The invention also provides a carrier protein-like polypeptide lacking the natural glycosylation of the carrier protein.

The invention is also a therapeutic composition for inhibiting the effect of somatomedin-C in acromegaly, for inhibiting the growth of retinal blood vessels and fibrous tissues in diabetic retinopathy, for inhibiting growth of tall children, for inhibiting the growth of keloid scars, for inhibiting the growth of tissue in the orbit of the eyes in malignant exophthalmos or for stimulating the healing of human or animal wounds, comprising an effective amount of at least one such carrier protein-like polypeptide described above, or a pharmacologically-acceptable salt thereof, and a pharmacologically-acceptable carrier. The invention includes a method for inhibiting the growth of somatomedin-dependent cancers, for inhibiting the effect of somatomedin-C in acromegaly, for inhibiting the growth of retinal blood vessels and fibrous tissues in diabetic retinopathy, for inhibiting growth of tall children, for inhibiting the growth of keloid scars, for inhibiting the growth of tissue in the orbit of the eyes in malignant exophthalmos or for stimulating the healing of human or animal wounds, comprising administering an effective amount of such a composition.

The invention is also embodied in a composition having at least one such carrier protein-like polypeptide described above substantially complexed with at least one somatomedin-like polypeptide. Such compositions may be used in a therapeutic composition for treating osteoporosis in humans, for stimulating the growth of bone, for stimulating animal growth, for stimulating the healing of human and animal wounds, or for stimulating the growth of patients with growth hormone deficiency, comprising an effective amount of such a composition. Such compositions may also be used in a method for treating such conditions comprising administering an effective amount of such a composition.

The invention provides a recombinant DNA molecule having a DNA molecule including a gene which codes for such a carrier protein-like polypeptide linked to an expression control sequence and having a DNA molecule including a gene which codes for a somatomedin-like polypeptide operatively linked to an expression control sequence. A host may be transformed with at least one such recombinant DNA molecule to permit it to produce both types of polypeptides.

A single vector may also be constructed to contain a DNA molecule which codes for at least one carrier protein-like polypeptide described above and a DNA molecule which codes for a somatomedin-like polypeptide each operatively linked to an expression control sequence. A host may be transformed with such a vector. A method for producing a composition comprising a complex of a carrier protein-like polypeptide and a somatomedin-like polypeptide involves transforming an appropriate host with such a vector and culturing said host to make said polypeptides. That method could include the additional step of collecting the polypeptides. That method could comprise simply culturing a host transformed with such a vector. A method for producing such a composition also involves transforming an appropriate host with at least one recombinant DNA molecule or vector having a DNA molecule which codes for a carrier protein-like polypeptide as described above, co-transforming such host with at least one recombinant DNA molecule or vector having a DNA molecule which codes for a somatomedin-like polypepide, and culturing such host to produce both types of polypeptides. The invention also encompasses hosts transformed with at least one of each such type of recombinant DNA molecule or vector.

Finally, monoclonal and polyclonal antibodies against such polypeptides may be produced. The polypeptides of the invention could also be used in a method for measuring the level of free somatomedins in human fluids comprising separating somatomedins complexed with such polypeptides from unbound somatomedins.

BRIEF DESCRIPTION OF THE DRAWINGS

FIG. 1 shows the sequence of the N-terminal 42 amino acid residues of a human carrier protein subunit having a molecular weight of about 15,000 daltons. In addition, the N-terminal sequences of tryptic fragments T1, T6, T7, T1, and T10 are shown.

FIG. 2a shows the sequence of the N-terminal 57 amino acids of the subunit referred to in FIG. 1, and an oligonucleotide coding for amino acids 29–44, designed for use as a probe. This oligonucleotide is referred to as the 48mer.

FIG. 2b shows the protein and DNA sequence of the 181-bp synthetic DNA and its corresponding protein sequence.

FIG. 4 displays the nucleotide sequence of the coding strand of DNA molecule LCP 2.3 and the amino acid sequence of the 291 amino acids of the polypeptide for which it codes. "C" indicates a cysteine or half-cystine residue.

ASSAY FOR SOMATOMEDIN BINDING ACTIVITY

Figure 3A:
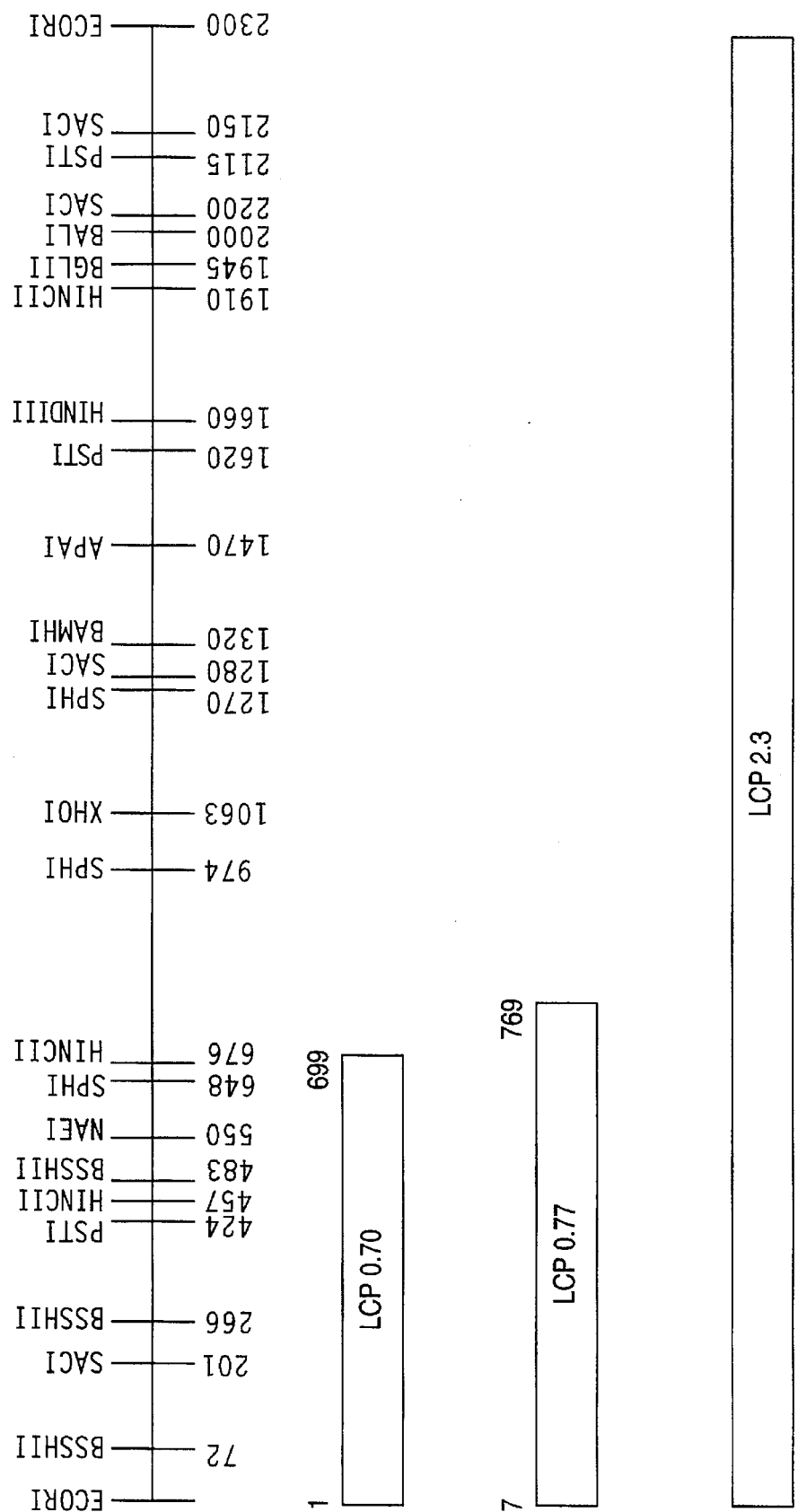
FIG. 3a shows the size and restriction sites of the DNA inserts LCP 0.70 and LCP 0.77 that hybridized, to the probe of FIG. 2a, and the size and restriction sites of a DNA insert LCP 2.3 that hybridized to probes having the DNA sequences of those DNA inserts LCP 0.70 and LCP 0.77.

The somatomedin binding activity is measured by a protein binding assay employing a radiolabeled $^{125}$I-SM (SM-C or IGF-II) as the ligand. The amount of $^{125}$I-SM bound is compared to that of a standard preparation.

The standard was prepared by gel filtration of a pool of human serum from 10 normal donors. The serum, 35 ml, was added to 35 ml of 4N acetic acid. After clarification, the sample was chromatographed on Sephadex G-50 (5×100 cm) (fractionation range 1,500 to 30,000) equilibrated with 1M acetic acid at a flow rate of 80 ml/hr. All fractions were assayed for somatomedin binding activity using $^{125}$I-SM-C. The binding activity appeared from $K_d$ 0–0.4. These fractions were lyophilized, redissolved in 1M acetic acid and rechromatographed to remove all traces of bound SMs. The final powder was redissolved in 35 ml of 0.1M phosphate buffer pH 7.0, aliquoted in 100 ul amounts, and stored at $-26°$ C. For each binding assay, a tube of this material was used as a reference that has arbitrarily been assigned a value of 1.0 U/ml.

The assay method was that described by Zapf et al., ("Serum Levels of the Insulin-like Growth Factor (SM) and its Carrier," *Acta Endocrinol.* 95, p. 505–517, (1980)). For samples where the carrier protein subunit was still complexed to SMs, the two were separated by Sephadex G-50 chromatography (0.9×110 cm) in 1M acetic acid. The binding activity peak ($K_d 0.1–0.4$) was then lyophilized, reconstituted in assay buffer and tested. For samples that did not contain bound SMs, the samples were either dialyzed against assay buffer and tested directly or, if the concentration of binding activity was low, dialyzed vs 0.1M acetic acid, lyophilized and dissolved in a smaller volume of assay buffer. The assay buffer was 0.1M sodium phosphate pH 7.0 containing 0.2% human or bovine serum albumin which had been previously tested to ensure absence of competing activity. SM-C or IGF-II were iodinated by the method of Spencer. Grecu, E. O., E. M. Spencer, et al., "Serum Somatomedin Response to Human Growth Hormone Infusion in Patients with Diabetes Mellitus: Correlation with the Degree of Control of Diabetes," Am. J. Mad. Sci., 287, pp. 7–10 (1984). Serial dilutions (2-or 4-fold) of samples and standard were assayed in triplicate. Assay tubes consisted of 100 ul of $^{125}$I-SM, 20,000 cpm, and 200 ul of the sample. The assay was carried out at 4° C. for 16 h although satisfactory results could be obtained with a 2 h incubation at room temperature. The bound $^{125}$I-SM was separated from the free by charcoal extraction. An ice cold solution, 0.8 ml, of 2% activated charcoal with 1% human (or bovine) albumin in 0.1M phosphate buffer pH 7.0 was added and the tubes vortexed for 15 minutes at 4° C. After centrifugation, the supernatant was counted. The cpm bound were plotted against the log of the dose and the potency of the unknown related to that of the standard assigned a value of 1.0 U/ml. The specificity of binding was determined by incubating the sample with a large excess of an unlabeled SM.

Other Somatomedin Binding Assays

Dot-blot and Western assays may also be used to determine the existence of polypeptides with somatomedin binding activity.

Dot Blot "Binding In Wells" Format

The nitrocellulose membrane and 3-MM filter paper are first placed in water and subsequently soaked in PBS (10 mM $NaPO_4$, pH 7.2, 0.15M NaCl) for 20–30 minutes. The filter paper and membrane are placed on the dot-blot apparatus, with the membrane on top of the filter paper. The apparatus is assembled and clamped according to manufacturer's instructions (Bio-Rad). The dot-blot apparatus contains 96 wells which makes it very convenient to process many samples simultaneously. Wells are rinsed with 200 ul PBS. Carrier protein-like polypeptides are diluted in PBS to the appropriate concentrations to make total volumes of 50 ul/well. Control and blank wells contain BSA (bovine serum albumin) or no protein, respectively. Samples are applied to wells and are allowed to flow through the membrane by gravity. Binding of the protein to the membrane is completed within 30–60 minutes. The membrane is blocked with 200 ul/well 1% BSA in PBS, which is allowed to flow by gravity for 30 minutes, then is "pulled" by a vacuum through the membrane. Wells are washed three times with 100 ul TBS (50 mM Tris-HCl, pH 7.5, 0.15M NaCl ), 0.1% Tween 20. $^{125}$I-SM-C (20,000–200,000 cpm) is added in 50 ul PBS per well. The apparatus is tightly covered with Parafilm and left at 4 for 1.5–2 hours. This step constitutes the binding of SM-C to carrier protein-like polypeptides. The apparatus is disassembled and the membrane washed in large volumes of TBS: TBS, 0.1% Tween 20: and TBS; each wash is 15 minutes at 4° C. with gentle shaking. The membrane is air dried and exposed to Kodak X-Omat AR film with intensifying screens at −70° C. for 1–6 hours, Dot Blot "Binding in Bag" Format Pretreatment of membrane, dot-blot apparatus assembly, and binding of protein to membrane is carried out as described above. Following binding of protein to membrane, the dot-blot apparatus is disassembled, and the membrane is air dried. The membrane is placed in a dish and washed at 4 with gentle shaking in the following solutions: TBS plus 3% NP40, for 30 minutes; TBS plus 1% BSA, for 1 hour; TBS plus 0.1% Tween 20, for 10 minutes. The membrane is placed in a bag with 6–10 ml binding solution (TBS, 1% BSA, 0.1% Tween 20). $^{125}$I-SM-C (2–20 million cpm) is added and binding proceeds at 4° C. for 2 hours or overnight, with gentle shaking. This step constitutes the binding of SM-C to carrier protein-like polypeptides. The membrane is washed two times in large volumes of TBS, 0.1% Tween 20 and two times in TBS alone. Each wash is done for 15 minutes at 4° C., with gentle shaking. The membrane is air dried and exposed to Kodak X-Omat AR film with intensifying screens at −70° C. for 5–16 hours.

Western

Protein samples containing carrier protein-like polypeptides are loaded and run on polyacrylamide-SDS gels. Normally 12% gels are run which will allow for good separation of proteins between 10,000 and 70,000 daltons. Separation is accomplished by electrophoresis. Proteins within the gel are then blotted onto a nitro-cellulose membrane, and the resultant membrane is air dried 5 minutes at 37° C. The membrane, containing the bound proteins, is rinsed with TBS plus 3% NP40 at 4° C. for 30 minutes. The membrane's nonspecific sites are blocked with 1% BSA in TBS at 4° C. for 2 hours. The membrane is rinsed with TBS plus 0.1% Tween 20 at 4° C. for 10 minutes. The membrane is probed with $^{125}$I-SM-C by placing the membrane in a bag with 6–10 ml TBS, 1% BSA, 0.1% Tween 20 plus 500,000 cpm $^{125}$I-SM-C. The membrane is gently shaken overnight at 4° C. to allow for binding between SM-C and carrier protein-like polypeptides immobilized on the membrane. The membrane is subjected to the following washes at 4° C.: TBS plus 0.1% Tween 20, twice, for 15 minutes each; TBS, three times, for 15 minutes each. The membrane is air dried and exposed to Kodak X-Omat AR film with intensifying screens at −70° C. for 5–16 hours.

Process For Producing Carrier Protein Subunits From Plasma

The procedure for producing the carrier protein subunits began with Cohn fraction IV-1. This is a human plasma fraction that contains about 10% of the plasma proteins and 40% of the original plasma carrier protein activity. It is a green-yellow paste, approximately 35% solids, much of which are denatured insoluble proteins and glycoproteins. Each kilogram of this paste contains approximately 10 mg of carrier protein.

All assay buffers described below contained the following enzyme inhibitors, unless otherwise noted: 1 millimolar ("mM") phenylmethylsulfonyl fluoride ("PMSF"), 1 mM N-ethylmaleimide ("NEM"), and 1 mM ethylenediaminetetraacetic acid ("EDTA"). Enzyme inhibitors were essential because either the carrier protein has inherent protease activity or at least one other plasma protease was co-purified through the affinity chromatography step.

EXAMPLE 1

(a) Ion Exchange Chromatography

Fraction IV-1 was handled in 1 kg batches. One kg of fraction IV-1 was added to 10 liters of 40 mM ammonium acetate-acetic acid solution pH 5.65 containing enzyme inhibitors and stirred overnight at 4° C. The suspension was centrifuged and the supernatant was concentrated to about 1 liter by ultrafiltration with a 10,000 MW semipermeable membrane.

The entire concentrate was applied to a 10×25 cm column at 4° C. of a sulfopropyl derivative of cross-linked dextran (SP-Sephadex, Pharmacia) previously equilibrated with 40 mM ammonium acetate-acetic acid buffer at pH 5.65. The column was washed with 5 liters of the same buffer, followed by 10 liters of 50 mM ammonium acetate pH 6.8, and finally 2 liters of 50 mM ammonium acetate-ammonia at pH 9.6. The pH 9.6 eluate was collected and lyophilized. The recovery of SM binding activity in the lyophilized material determined by the binding assay was 20%. This constituted about a 10 fold purification.

(b) Hydrophobic Interaction Chromatography

The lyophilized product with SM binding activity was dissolved in a buffer containing 10% ammonium sulfate and 50 mM tris-(hydroxymethyl) aminomethane ("Tris")-hydrochloride ("Tris-HCl") pH 7.5, dialyzed against the same buffer, and applied to a phenyl agarose column (Phenyl-Sepharose, Pharmacia). The column was eluted first with 1 liter of the same buffer, then with 2 liters of 50 mM Tris-HCl pH 7.5 containing 0.5M sodium thiocyanate ("NaSCN") and finally with 2 liters of 50 mM Tris, pH 9.0. The eluted fractions were collected and tested for UV absorption at 280 nM and for SM-binding activity in the binding assay. The SM binding activity appeared in the NaSCN fractions. These were lyophilized and then dialyzed against distilled water. A significant amount of precipitate appeared which was separated from the supernatant. This step resulted in a 20-fold purification with 70% recovery.

(c) Gel Filtration

The supernatant was lyophilized, dissolved in 0.5M acetic acid and chromatographed on a 2×100 column of a cross-linked dextran gel (Sephadex G-150, Pharmacia) having a fractionation range of 5,000–230,000. Fractions containing SM binding activity were collected. The recovery of SM binding activity was 80–90% by binding assay and the fold purification was 5.

(d) Affinity Chromatography

A SM-C affinity column was first made by coupling SM-C previously purified from human plasma (Spencer et al., in *Insulin-Like Growth Factors/Somatomedins*, ed. Spencer, E. M., Walter de Gruyter 1983), p. 81) to a hydroxysuccinimidyl derivative of agarose (Affi-Gel 15, BioRad) at pH 8.0 and 25° for 2 hours. The combined carrier protein fractions from the previous step were dialyzed against 0.1M sodium phosphate pH 7.0, then applied to the SM-C affinity column. After a 15 ml wash with the see buffer, the SM binding activity was eluted with 10 ml of 0.5M acetic acid and lyophilized.

The SM binding activity was next chromatographed on a cross-linked dextran gel (Sephadex G-100, Pharmacia) having a fractionation range from 4,000–90,000 and eguilibrated with 0.5M acetic acid. The fractions containing activity, as shown by the SM binding assay, were lyophilized.

(e) High Performance Liquid Chromatograph("HPLC")

The lyophilized material was chromatographed by HPLC on a butylsilane (Vydac $C_4$ RP (reverse phase)) column. The SM binding activity was eluted by a 0–60% linear gradient of acetonitrile in 0.1% trifluroacetic acid ("TFA"). A sharp peak of SM-C binding activity occurred at 39% acetonitrile and was collected. The SM binding activity In this peak appeared as a single band on 12.5% sodium dodecylsulfate-polyacrylamide gel electrophoresis ("SDS-PAGE") upon staining with a silver stain (BioRad).

The carrier protein subunit isolated had a molecular weight of approximately 26 kDa as shown by SDS-PAGE in the presence of β-mercaptoethanol. The overall yield of the carrier protein subunit was 4% of the original binding activity.

The N-terminal amino acid molecule of this carrier protein subunit was determined by the method of Hunkapillar and Hood (Methods in Enzymology, 91, p. 486, (1983)), using an automated gas phase sequenator (Beckman 6300) to be:

Gly—Ala—Ser—Ser—Ala—Gly—Leu—Gly—Pro—Val—
Val—Arg—R—Glu—Pro—R—Asp—Ala—Arg—Ala—
Leu—Ala—, with R indicating cysteine or half-cystine. This carrier protein subunit bound 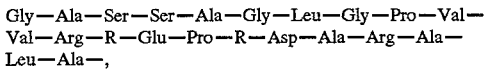$^{125}$I-SM-C and was shown to be glycosylated by periodic acid Schiff ("PAS") staining.

EXAMPLE 2

(a) Ion Exchange Chromatography

One kg of Cohn fraction IV-1 was extracted with 4 liters of 40 mM ammonium acetate-acetic acid buffer pH 5.65 with inhibitors (1 mM EDTA. 1 mM NEM, 0.1 mM PMSF and 1 mg/1 aprotinin) overnight at 4° C. The protein solution was spun at 9,000×g for 30 minutes to separate precipitate from supernatant. The precipitate was reextracted with 4 liters of the above buffer for 4 hours. Supernatants from both extractions were combined.

The supernatants were applied to a SP-Sephadex column (2000 ml resin) which had been equilibrated with the above buffer at 4° C. After application, the column was washed with the same buffer until the $A_{280}$ dropped below 1.0. The column was further washed with 50 mM ammonium acetate buffer. pH 6.8 with inhibitors until the $A_{280}$ was below 1.0. Then the SM binding activity was eluted with 60 mM ammonium acetate-ammonia buffer, pH 9.6 with inhibitors. Finally, the column was cleaned with 60 mM ammonium acetate-ammonia, pH 9.6 with 1.0M NaCl.

The extract from 1 kg Cohn fraction IV-1 gave about 5,000 units of SM-binding activity. In the pH 9.6 fractions about 7.5% of the activity was recovered, as determined by the binding assay. The weight of the fraction was approximately 5.5 g.

(b) Ion Exchange Chromatography

The pH 9.6 fraction from the previous column was dissolved in 130 ml of a 1M acetic acid solution containing inhibitors (0.1 mM EDTA, PMSF, NEM and 1 mg/l aprotinin). The solution was dialyzed at 4° C. overnight against the same buffer solution and applied to a 5×40 cm SP-Sephadex column, which had been previously equilibrated with the same buffer. The column was washed until $A_{280}$ was approximately 0.2, then eluted with 60 mM ammonium acetate-ammonia, pH 9.6, with inhibitors. The SM binding activity was in the pass-through fraction which was dialyzed at 4° C. against distilled water overnight to precipitate some denatured proteins. After dialysis, the precipitate was removed by centrifugation at 9,000×g for 30 minutes and the supernatant freezed-dried. SM binding activity was recovered quantitatively in the soluble pass-through fraction, while SM-C was recovered in the pH 9.6 fraction.

(c) Gel Filtration

An aliquot of the fraction (0.33 g) containing SM binding activity was then dissolved in a minimal amount of 0.5M acetic acid solution and applied to a 2.5×100 cm Sephadex G-100 column, which had been equilibrated under the same conditions. The column was eluted with 0.5M acetic acid. The $A_{280}$ and SM binding activities of 5 ml fractions were measured. Those fractions exhibiting activity were pooled together and lyophilized. The purification was at this step five fold and the SM binding activity was recovered quantitatively. Several runs were required to process all the material.

(d) Affinity Chromatography

Eighty mg of fractions containing binding activity from the previous step were dissolved in 40 ml of 0.1M phosphate buffer, pH 7.0, with inhibitors and dialyzed against the same buffer for about 4 hrs. After dialysis, the solution was mixed with 3 ml SM-C-affinity column resin. The mixture was agitated gently at 4° C. overnight to increase the binding. The resin was separated from the protein solution by passage through a column. The column was first washed with 50 ml of the phosphate buffer then eluted with 0.5M acetic acid. The SM binding activity (about 10 units) was dried in a vacuum centrifuge (Speed-Vac Concentrator, Savant Instruments).

(e) HPLC

The 10 units of recovered SM binding activity were dissolved in 1 ml 0.1% TFA solution. After injecting the sample onto a Vydak C4 RP column, the column was eluted with a 0–60% acetonitrile gradient in 60 minutes. The carrier protein peak appeared at approximately 39% acetonitrile, which was collected and lyophilized. The SM binding activity was recovered quantitatively and was approximately 60 micrograms.

The SM binding activity appeared after silver staining as m single band on SDS-PAGE, with a molecular weight of about 15 kDa. The overall yield of this example was approximately 3%.

The specific activity of the pure carrier protein subunit was determined to be 4 ug/unit where 1 unit is the amount in 1 ml of a standard plasma prepared from m pool of 10 normal men and women, as described above.

For N-terminal molecule determination, the SM binding activity was denatured and reduced in 4M quanidine-HCl, 0.5M Tris-HCl, pH 8.6 and 0.7% β-mercaptoethanol overnight. Iodoacetamide was added to the solution. The reaction was carried out in the dark for one hour and stopped by adding TFA to 0.1%. The reaction mixture was injected onto the HPLC column and the carboxyamidomethylated carrier protein subunit recovered as before and used for N-terminal molecule analysis. That analysis showed the same N-terminal amino acid molecule described in the example 1.

EXAMPLE 3

The carrier protein subunit was purified as in Example 2 through the gel filtration step (c). A 30 mg aliquot of the resulting sample containing SM binding activity was dissolved in 0.1% TFA solution and injected into a preparative Vydak C4 RP column. The column was eluted with a 0–60% acetonitrile gradient in 60 minutes. The SM binding activity peak which eluted at approximately 39% acetonitrile was collected and lyophilized. The SM binding activity was recovered quantitatively.

The sample was subsequently resuspended in a Tris-glycine buffer containing β-mercaptoethanol and separated by SDS-PAGE (12.5% polyacrylamide). Bands corresponding to 15, 21, 26, and 30 kDa carrier protein subunits (each of which bound labelled SM in a Western blot) were cut from the gel, and the proteins were electroeluted into Tris-glycine buffer. Each of the carrier protein subunits was lyophilized; recoveries were quantitative.

EXAMPLE 4

Experiments designed to measure the potential of SM carrier protein subunits to potentiate wound healing were carried out in the following manner. Each of 6 anesthetized 300 gram male Sprague-Dawley rats was implanted subcutaneously (s.c.) with Schilling-Hunt wire mesh wound cylinders in each of the 4 quadrants on their back. Cylindrical chambers, 20×5.8 mm i.d. with a volume of 520 ul, were constructed out of stainless steel wire mesh. One end was sealed with wire mesh and the other with a silastic disk. After implantation, the typical progression of wound healing events occurred: thrombosis of blood vessels followed sequentially by migration through the wire mesh of polymorpho-nuclear leukocytes, macrophages and fibroblasts, with subsequent fibroplasia, collagen synthesis and angiogenesis. During this process, the wound fluid that collected in the hollow chamber could be sampled or injected with active agents (s.c. through the silastic disk). Most of the healing was complete by 17 days after implantation: however, the central cavity was never completely obliterated.

The 15 kDa SM carrier protein subunit was dissolved in PBS (150 mM sodium chloride, 10 mM sodium phosphate, pH 7.4), containing 0.1% bovine albumin. The wound chambers were injected with 100 ul of this solution (containing 1.4 ug of the 15 kDa species) every 12 hours. This amount was selected to be only slightly in excess of the Mount of biologically active somatomedins and thereby increase the half-life of somatomedins present. After 17 days, wound cylinders were removed, and the fibrous tissue was scraped carefully from each cylinder. Cylinders injected with 15 kDa carrier protein subunit material were all filled with dense fibrous tissue that was considerably greater than that in the controls. Specifically, 19.5±7 (SD) mg of protein were deposited in wound chambers containing 15 kDa carrier protein subunit as compared to 7.0±1.6 mg deposited in controls. DNA synthesis was also much greater in carrier protein subunit-containing chambers (1160±200 ug vs 380±15 ug in controls). Likewise, hydroxyproline levels (an indicator of collagen synthesis) were significantly higher in carrier protein subunit-containing chambers (460 ug vs 270 ug in controls).

These results demonstrate that injection of 15 kDa carrier protein subunit into wound chambers markedly augments the rate of healing.

EXAMPLE 5

An animal experiment was conducted to show that the carrier protein subunits increase the serum half-life of SM-C. The 15 kDa human carrier protein subunit was shown to prolong the half-life of purified human SM-C injected into a rat's bloodstream.

The complex between the 15 kDa carrier protein subunit and $^{125}$I-SM-C was formed by incubating $^{125}$I-SM-C with the carrier protein subunit overnight at 4° C. in PBS (10 mM sodium phosphate, pH 7.25, 150 mM sodium-chloride). The complex was separated from free $^{125}$I-SM-C by gel filtration. Specific activity of the $^{125}$I-SM-C was 6.7×10⁵ cpm per ug.

Rats (about 200 grams) were anesthetized and catheterized through the Jugular vein. Prior to injections, the catheters and syringes were rinsed with 4% BSA (bovine serum albumin) to prevent sticking of the proteins to plastic surfaces. Four rats received BSA, four rats received 2 ug $^{125}$I-SM-C alone, and four rats received 2 ug $^{125}$I-SM-C complexed with 15 kDa carrier protein subunit. Both the complex and the SM-C were in PBS. One rat received 1 ug $^{125}$I-SM-C complexed with the carrier protein subunit. Blood samples (100–200 ul) were removed at multiple time points post injection. Blood cells were immediately separated from the plasma by centrifugation. A 25 ul plasma aliquot was counted to determine the concentration of $^{125}$I-SM-C present and a 10 ul aliquot was run on a 15% polyacrylamide-SDS gel to determine SM-C integrity. Injections were carried out over a two day period. Each morning 2 rats were injected with the complex and 2 rats with SM-C alone. On a third day, 4 control rats were injected with BSA.

Figure 9:
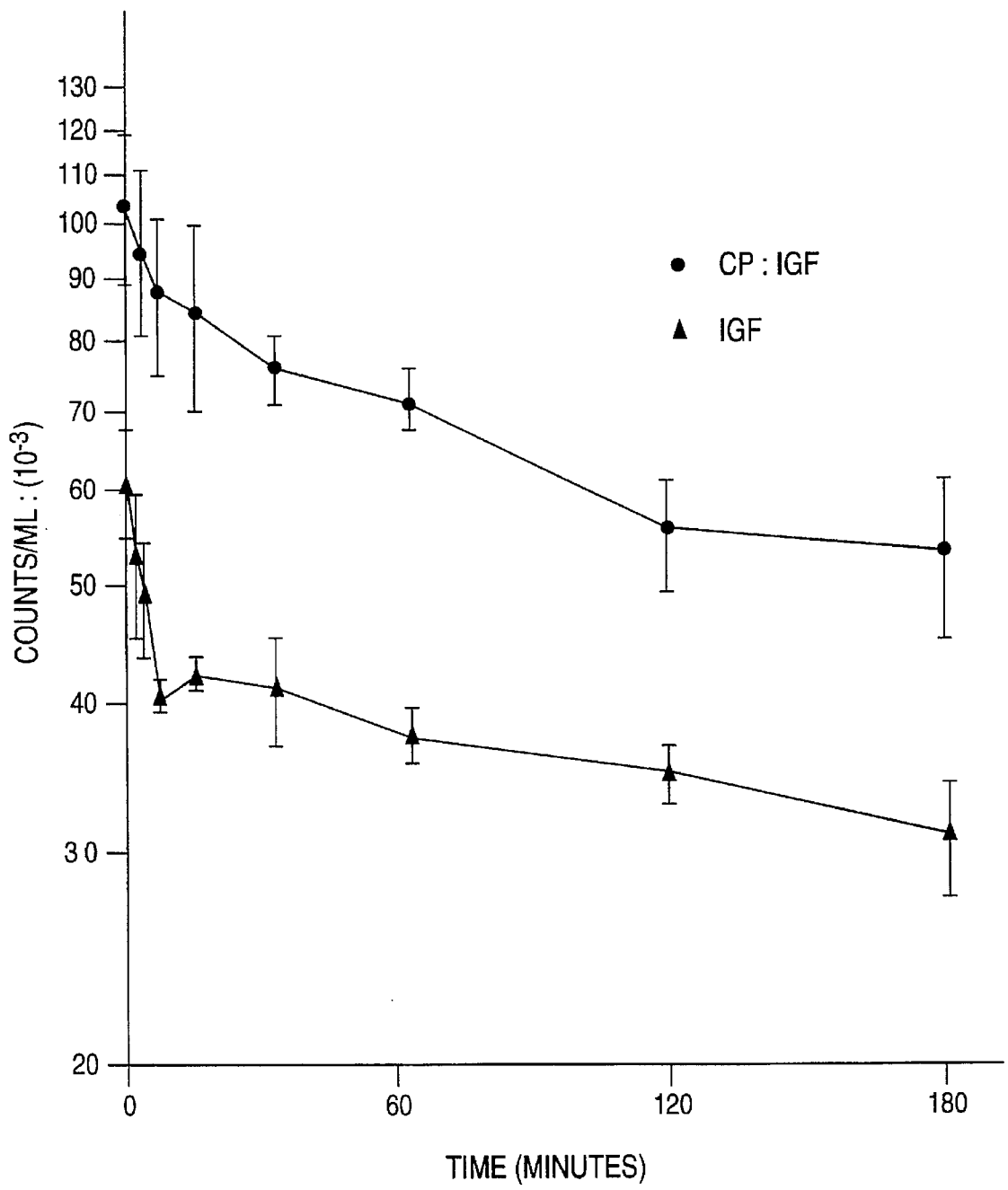
FIG. 9 shows the effect of 15 kDa carrier protein subunit on the half-life of SM-C in circulation.

This study demonstrates that the 15 kDa carrier protein subunit significantly increases the half-life of SM-C in the circulation. An equal number of counts (i.e., 1.3×10⁵ cpm/ml rat blood) of SM-C was added to rats either alone or complexed with the carrier protein subunit. As shown in FIG. 9, a majority of free SM-C is rapidly removed from the circulation, whereas the carrier protein subunit protects SM-C from that removal. (Samples run on 15% SDS [sodium dodecyl sulfate] polyacrylamide gels indicated that all $^{125}$I counts were SM-C; that is, there is no free $^{125}$I interfering with the experiment.) The continued appearance of the residual amount of free SM-C after 7.5 minutes may be due to SM-C occupying unsaturated rat carrier protein subunit molecules. Obviously, there were not sufficient endogenous carrier protein subunits to bind even 30% of all the free SM-C injected. It should be noted that there are not sufficient endogenous unsaturated carrier protein subunits in rats or in humans to be therapeutically useful. Thus, SM-C must be administered complexed to its carrier protein subunit.

Recombinant DNA And Carrier Protein-like Polypeptides

Preparation Of Oligonucleotide Probes Based On Protein Sequence Information

The carrier protein contains subunits that may be isolated and retain the capability of binding somatomedins, including subunits having apparent molecular weights, if glycosylated, of about 15, 21, 26, 30 and 45 kDa, and significantly less, if not glycosylated or subjected to other post translation modifications. If the N-terminal sequences of the subunits are the same, and the various subunits are encoded by the same gene or genes, then it should be possible to prepare a probe based on a common N-terminal sequence to identify DNA coding for carrier protein-like polypeptides. A carrier protein subunit was isolated and purified as described in Example 2, identified as S-15. The protein, S-15, was carboxymethylated and subjected to N-terminal sequence analysis using an Applied Biosystems Gas Phase Protein Sequencer, Model 470, by automated Edman degradation. The first 42 amino acids are in FIG. 1. In addition, the subunit S-15 was cleaved with the protease trypsin which specifically cleaves after arginines and lysines, unless lysine is followed by proline. Specifically, carboxymethylated S-15 was digested with trypsin in 0.3M sodium bicarbonate, pH 8.0. Tryptic fragments were separated by reverse phase HPLC using a Vydac C₄column. Purified fragments were collected and sequenced as described above. The sequences of several such tryptic fragments, denoted as T-1, T-6, T-7, T-1', and T-10, are also shown in FIG. 1. Due to the homology between the amino terminus and tryptic fragment T-7, it was determined that the first 57 N-terminal amino acids of subunit S-15, with two undetermined amino acids, are as shown in FIG. 2a.

Many oligonucleotides were designed from this molecule to serve as probes to screen cDNA libraries. These included short degenerate probes and long codon biased probes. One oligonucleotide corresponding to a portion of the N-terminal 57 amino acid molecule identified as the 48mer, is shown in FIG. 2a.

Selection Of Tissues For Preparation of PolyA⁺ RNA Containing Carrier Protein mRNA The strategy utilized to isolate carrier protein genes was to identify a tissue making large quantities of carrier protein, isolate mRNA from that tissue, construct a cDNA library from that mRNA, and screen for the gene using oligonucleotide probes. The hope was that an enriched cDNA library would contain more copies of such a gene than would a genomic (total DNA) library which will only contain perhaps one copy. There was no information in the literature to establish which tissue or cell type makes the carrier protein, a protein which is found in the serum. Fibroblasts had been shown to produce small amounts of a large but otherwise uncharacterized somatomedin binding protein (Adams, et supra). However, it is known that the majority of SM-C is synthesized in the liver. In addition, SM-C is synthesized by fibroblasts and other tissues such as the heart, bone, placenta, and kidney. Therefore, speculating that SM-C and the carrier protein would be synthesized by the same tissues, the liver and fibroblast cells were chosen as two potential sources of the mRNA coding for the carrier protein.

In order to identify a tissue or cell line source of such mRNA, RNAs isolated from several human livers were prepared and tested for their ability to direct the synthesis of carrier protein. In addition, various fibroblast cell lines were assayed for their ability to make carrier protein.

Preparation Of PolyA⁺ containing RNA

Total and polyA⁺ containing RNA were isolated from various liver tissues and fibroblast cells according to standard procedures (Chirgwin, J. M., Pryzbyla, A. E., MacDonald, R. J. & Rutter, W. J. (1979) Biochemistry 18, 5294–5299 end Iversen, P. L., Mate, J. E. & Hines, R. N. (1987) BioTechniques 5, 521–523.). Either tissue (e.g., liver) or cells (e.g., fibroblasts) were homogenized in GIT buffer (4M guanidinium isothiocyanate, 20 mM EDTA, 100 mM Tris-HCl, pH 7.6). Debris was removed, and the RNA-containing supernatant was brought to 2% Sarkosyl (sodium laurel sarkosinate) and 1% β-mercaptoethanol. The mixture was then centrifuged through a cesium chloride gradient. Pellets were resuspended and extracted with phenol and chloroform and subsequently precipitated with ethanol. PolyA⁺ RNA, which represents the mRNA, was purified from total RNA by passing total RNA over an oligo-dT cellulose column (Aviv. H. & Leder, P. [1972] PNAS 69:1408). The resulting polyA⁺ containing RNA was eluted from the column with 10 mM Tris, pH 7.4, 1 mM EDTA, 0.05% sodium dodecyl sulfate (SDS), concentrated, and stored for further use. The liver polyA RNAs were assigned the names H10 and H14, indicative of the liver sample from which they were purified, and the fibroblast cell polyA⁺ RNAs assigned the code name WI38, HS27, MRC5, 8387, and MDA-MB-231 indicative of the cell source of the RNA.

Testing Of RNA For Translation Products

An aliquot of human liver polyA⁺ RNA from H10 and H14 were translated in vitro using a rabbit reticulocyte translation kit with $^{35}$S-methionine according to standard procedures (Davis, L. G., et al., "Basic Methods in Molecular Biology," (Elsevier, New York, N.Y., 1986)). The protein translation products were immunoprecipitated (according to Davis) with an antibody provided by Robert C. Baxter (Royal Prince Alfred Hospital, Australia), prepared in accord with Martin, J. L., et al. "Antibody Against Acid-Stable Insulin-like Growth Factor Binding Protein . . . ", J. Clin. Endocrinol. Metab., 261, pp. 799–801 (1985). That antibody was raised against material containing the so-called acid-stable subunit of the carrier protein obtained from human serum. Immunoprecipitated proteins were analyzed by SDS-polyacrylamide gel electrophoresis. Protein bands of about 68,000, 43,000, 39,000 and 32,000 daltons were identified that reacted specifically with anti-carrier protein subunit antibody. The proteins were not precipitated by a control serum, which did not contain anti-carrier protein subunit antibodies. This result suggested that carrier protein is being made by a liver and that a cDNA library made from liver mRNA should contain the carrier protein gene.

Several fibroblast cell lines were also tested for their ability to produce the carrier protein. For example, WI38 embryonic fibroblasts (American Type Culture Collection No. CCL-75) were grown to 70–80% confluence in DMEM-F12 media containing 10% fetal calf serum. Cells were switched to serum free media and incubated for 72 hours. Culture supernatants were harvested and concentrated by TCA precipitation or by centrifugation. Samples were subjected to SM-Western analysis (SDS-PAGE step being carried out under non-reducing conditions) which demonstrated that WI38 cells synthesized and secreted at least 4 proteins capable of binding SM-C, in the size range of 25,000–45,000 daltons. Of these, an about 40,000 dalton protein (by reducing SDS-PAGE) was also specifically recognized by the anti-carrier protein subunit antibody. In this experiment, the 72 hour incubation of WI38 cells in serum free medium included the addition of $^{35}$S-cysteine. The proteins were immunoprecipitated with anti-carrier protein subunit antibody and analyzed by SDS-PAGE under reducing conditions.

Other cell lines encoding carrier protein subunits that were both recognized by anti-carrier protein subunit antibody and bound by SM-C include HS27 (human fibroblast), MRC5 (human fibroblast), 8387 (human fibrosarcoma), and MDA-MB-231 (human breast cancer). It is expected that polyA⁺ RNA isolated from other fibroblast lines would also encode carrier protein.

It should be recognized that the polyA⁺ RNA product obtained from these sources contain a very large number of different mRNAs. Except for the mRNA specific for carrier protein or carrier protein subunits, the other mRNAs are undesirable contaminants. Unfortunately, these contaminant RNAs may behave similarly to carrier protein subunit mRNA throughout the remainder of the cloning process of this invention. Therefore, their presence in the polyA⁺ RNA will result in the ultimate preparation of a large number of unwanted bacterial clones, which contain genes that may code for polypeptides other than carrier protein. This contamination presents complex screening problems in the isolation of the desired carrier protein hybrid clones. In the case of carrier protein, the screening problem was further exacerbated by the lack of a sufficiently purified sample of carrier protein mRNA or DNA, or portion thereof, to act as a screening probe for the identification of the desired clones. The only available probes were those based on the limited N-terminal protein molecule information. Therefore, the screening process for the carrier protein clones is very time-consuming and difficult. Furthermore, because only a very small percentage of carrier protein clones themselves are expected to express carrier protein-like polypeptide in a biologically or immunologically active form, the isolation of an active clone is a difficult screening process.

Synthesis Of Double Stranded cDNA Containing Carrier Protein cDNA

PolyA⁺ RNA containing carrier protein mRNA was used as a template to prepare complementary DNA ("cDNA"), essentially as described by Gubler and Hoffman. cDNA libraries were made from the mRNAs which had been shown to encode potential carrier protein-like polypeptides. The libraries were constructed in the λ vector gt10, but could be constructed in other vectors as well (e.g., λ gt11 [Young, R. A. & Davis, R. W. (1983) Proc. Natl. Aced. Sci. USA 80, 1194–1198]). Double-stranded cDNA was generated essentially according to the Gubler-Hoffman method (Gubler, U. & Hoffman, B. J. (1983) Gene 25, 263–269). In this protocol, first strand cDNA was synthesized using Moloney Reverse Transcriptase to copy the polyA⁺ RNA. Libraries described below include a random-primed human liver cDNA library (H14), two oligo-dT-primed human liver cDNA libraries (H14, H10/H14 [a pool of H10 and H14]), and an oligo-dT-primed human embryonic fibroblast library (WI38). Random primers (pd(N)$_6$) and oligo-dT (pT$_{12-18}$) primers were obtained from Pharmacia. The second strand was produced using a combination of RNAseH and DNA polymerase I.

The resulting cDNA population is in fact a complex mixture of cDNAs originating from the different mRNAs, which were present in the polyA⁺ RNA. In addition, because of premature termination by Moloney reverse transcriptase, many of the cDNAs are incomplete copies of the various mRNAs in the polyA⁺ mRNA.

Cloning Of Double-Stranded cDNA

A wide variety of host vehicle combinations may be employed in cloning or expressing the double-stranded cDNA prepared in accordance with this invention. For example, useful cloning or expression vehicles may consist of segments of chromosomal, non-chromosomal and synthetic DNA molecules, such as various known derivatives of SV40 and known bacterial plasmids, e.g., plasmids from E. coli including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and Filamenteous single-stranded DNA phages and vectors derived from combinations of plasmids and phage DNAs such as plasmids which have been modified to employ phage DNA or other expression control molecules or yeast plasmids such as the 2 μ plasmid or derivatives thereof. Useful cloning or expression hosts may include bacterial hosts such as E. coli HB 101, E. coli X1776, E. coli X2282, E. coli MRCI, E. coli LE392, E. coli C600 and strains of Pseudomonas, Bacillus subtilis, Bacillus stearothermophilus and other bacteria, yeasts and other fungi, animal, insect or plant cells. Of course, not all host/vector combinations may be equally efficient. The particular selection of host vehicle combination may be made by those of skill in the art after due consideration of the principles set forth herein without departing from the scope of this invention.

Furthermore, within each specific cloning or expression vehicle, various sites may be selected for insertion of the double-stranded DNA. These sites are usually designated by the restriction endonuclease which cuts them. These sites are well recognized by those of skill in the art. It is, of course, to be understood that a cloning or expression vehicle useful in this invention need not have a restriction endonuclease site for insertion of the chosen DNA fragment. Instead, the vehicle could be joined to the fragment by alternative means.

The cloning or expression vehicle or vector, and in particular the site chosen therein for attachment of a selected DNA fragment to form a recombinant DNA molecule, is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification, expression characteristics, such as the location of start and stop codons relative to the vector molecules, and other factors recognized by those of skill in the art. The choice of a vector and an insertion site for a particular gene is determined by a balance of these factors, not all selections being equally effective for a given case.

Although several methods are known in the art for inserting foreign DNA into a cloning vehicle or expression vector to form a recombinant DNA molecule, the method preferred for initial cloning in accordance with this invention is digesting λ gt10 with EcoRI. The double-stranded cDNA is then ligated to this λ gt10 DNA, after first adding EcoRI linkers to the cDNA molecules. The resulting recombinant DNA molecule now carries an inserted gene at the chosen position in the cloning vector.

Of course, other known methods of inserting DNA molecules into cloning or expression vehicles to form recombinant DNA molecules are equally useful in this invention. These include, for example, dA-dT tailing, direct ligation, synthetic linkers, exonuclease and polymerase-linked repair reactions followed by ligation, or extension of the DNA strand with DNA polymerase and an appropriate single-stranded template followed by ligation.

It should, of course, be understood that the nucleotide molecules of cDNA fragments inserted at the selected site of the cloning vehicle may include nucleotides which are not part of the actual gene coding for the desired polypeptide or may include only a fragment of the complete gene for the desired protein. It is only required that whatever DNA molecule is finally inserted, a transformed host will produce a polypeptide having a somatomedin regulating biological activity of the carrier protein and being capable of binding somatomedin-like polypeptides, or that the DNA molecule itself is of use as a hybridization probe to select clones which contain DNA molecules useful in the production of polypeptides having such biological and binding activity.

The cloning vehicle or expression vector containing the foreign gene is employed to transform a host so as to permit that host to express carrier protein-like polypeptides. The selection of an appropriate host is also controlled by a number of factors recognized by the art. These include, for example, compatibility with the chosen vector, toxicity of proteins encoded by the hybrid plasmid, ease of recovery of the desired protein, expression characteristics, safety and cost. A balance of these factors must be struck with the understanding that not all hosts may be equally effective for either the cloning or expression of a particular recombinant DNA molecule.

In the present synthesis, the preferred initial cloning vehicle is λ gt10 and the preferred initial restriction endonuclease site is EcoRI. The preferred initial host is E. coli.

EcoR1-restricted λ gt10 DNA (Promega) was ligated to EcoR1 linkered cDNA molecules prepared as described in Maniatis, T., et al., *Molecular Cloning: A Laboratory Manual*, (Cold Spring Harbor Laboratory, Cold Spring Harbor, N.Y., 1982) and Davis, L. G., et al., "Basic Methods in Molecular Biology," (Elsevier, New York, N.Y. 1986) ("Maniatis").

The hybrid DNA obtained after annealing is, of course, a large mixture of different recombinant DNA molecules and some cloning vehicles without inserted DNA molecules. However, each recombinant DNA molecule contains a cDNA segment at the EcoRI site. Each such cDNA segment may comprise a gene or a fragment thereof. Only a very few of the cDNA fragments code for carrier protein or a portion thereof. The vast majority code for one of the other proteins or portions thereof whose mRNAs were part of the polyA$^+$ RNA used in the process of this invention. It should also be understood that it is possible that none of the clones of the above-prepared library may permit the expression of carrier protein-like polypeptides. Instead, they may only be useful in screening for and identifying such a clone.

The resultant λ DNA vectors containing cDNA inserts were packaged into λ phage using a λ phage packaging kit (Stratagene ).

E. coli cells (e.g., C 600 hfl) were infected with the recombinant phage and plated onto enriched media plates. (e.g. LB). Plates were incubated at 37° C. until phage plaques were visible.

The phage plaques (clones) contain a variety of recombinant DNA molecules representing sized, complete or partial copies of the mixture of polyA$^+$ RNA obtained from the liver. Each of the majority of these plaques will contain a single recombinant DNA molecule. However, only a very few of these recombinant DNA molecules are related to carrier protein. Accordingly, the clones must be screened to select the carrier protein related clones from the others.

Screening For A Clone Containing Carrier Protein cDNA

There are several approaches to screen for clones containing carrier protein cDNA. These include, for example, RNA selection hybridization, differential hybridization; hybridization with a synthetic probe or screening for clones that produce the desired protein by immunological or biological assays. We have chosen hybridization with a synthetic probe as being the most convenient and promising method for primary clone screening.

There is no assurance that the recombinant DNA molecules and bacterial cultures transformed therewith, which are identified by hybridization with a probe, contain the complete carrier protein cDNA molecule or that the DNA molecule actually codes for carrier protein or will permit the clone to express a carrier protein-like polypeptide. However, the recombinant DNA molecules will certainly contain extensive nucleotide molecules complementary to the carrier protein subunit mRNA coding molecule. Therefore, the recombinant DNA molecule may at least be used as a source of a probe to screen rapidly other recombinant DNA molecules and clones transformed with them to identify further sets of clones which will contain an authentic or complete carrier protein subunit nucleotide coding molecule. These clones may then be analyzed directly for possible expression of polypeptides displaying the biological and binding activity of carrier protein. More importantly, the nucleotide molecule of the inserted DNA fragment of these hybrid plasmids and its amino acid translation product may be determined using conventional means and that DNA molecule used to construct appropriate expression vectors that permit the synthesis of carrier protein-like polypeptides in appropriate hosts transformed with them.

Oligonucleotide Probe Hybridization

The phage cDNA library was mixed with *E. coli* and plated onto LB (enriched media) plates. The plates were incubated at 37° C. until phage plaques were visible. Each plaque represents a clone of a unique λ gt10 phage containing a cDNA insert. Approximately 0.5–1.0 million phage plaques were analyzed per experiment.

Analysis was carried out by transferring the phage DNA of these plaques from the plates onto nitrocellulose filters (0.45 um pore diameter Schleicher and Schuell or Millipore), using standard techniques (Davis and Maniatis). Thus, the DNA pattern on the filter was a replica of the plaque pattern on the plate. After identification of inserts contained within phage DNA that hybridized to the probe, the filters can be matched with the plates and phage isolated.

An oligonucleotide probe, the 48mer, of 48 bases (shown in FIG. 2a) was used to screen the random-primed human liver cDNA library H14. The probe corresponded to the molecule spanning the nucleotides encoding amino acids Ala[29] through Leu[44] of the carrier protein subunit S-15. This single oligonucleotide was designed to maximize on bias for human codons.

Hybridization conditions were determined by binding the 48-base probe (48mer) to Southern blots of human genomic DNA from the placenta and of a 181-bp synthetic DNA encoding amino acids Gly[1] through Tyr[57] (shown in FIG. 2b) under different degrees of stringency. The final conditions for hybridization, which would allow for gene identification with minimal background, was 40% formamide. 5×SSPE (0.9M sodium chloride, 50 mM sodium phosphate, pH 7.4, 5 mM EDTA). 42° C.

Nitrocellulose filters containing replicas of the phage plaques from the random-primed H14 human liver cDNA library were hybridized with $^{32}$P-labelled 48mer using the hybridization conditions described above. Hybridization was usually carried out overnight, and the filters were rinsed several times in 0.1×SSC (15 mM sodium chloride, 1.5 mM sodium citrate, pH 7.0), 0.1% SDS at 45–50° C. prior to autoradiography. DNA's that hybridized strongly to the 48mer were identified by autoradiography and the corresponding phage plaques were isolated. Since the original plating of phage was done at a high density, a second round of plating and screening was required to isolate single plaques. This second round of screening also verified that the original isolated phage plaques did indeed hybridize to the 48mer. Single plaques were picked from the plates and the phage were allowed to sluts into phage buffer (100 mM NaCl, 10 mM MgSO$_4$, 50 mM Tris, pH 7.5, 0.01% gelatin). After removing the bacteria by centrifugation, these phage stocks were maintained at 4° C. Phage DNA was purified and characterized (i.e., restricted by restriction endonucleases such as EcoRI in order to determine insert size) following standard procedures (e.g., Maniatis). Inserts were frequently subcloned into smaller plasmids, such as pBR322 or pGEM, at the EcoRI site, using standard procedures.

A number of positive plaques were identified (48 per 600,000 plaques screened). Of these, 9 were chosen for further analysis. Two of these clones (designated cLCP 0.70 and cLCP 0.77), which were approximately 700 to 800 bp in size and which showed the most intense binding by the 48mer probe were cut into smaller fragments prior to sequencing.

Fragments hybridizing to the 48mer, which would be initial sequencing candidates were identified in the following manner, cDNA inserts LCP 0.70 and LCP 0.77 were cleaved with restriction endonuclease HaeIII. These fragments were separated by agarose gel electrophoresis, transferred to a nitrocellulose membrane, and probed with $^{32}$P-labelled 48mer probe. When HaeIII fragments were probed, only one fragment bound the 48mer. This 90 bp fragment was present in both clones LCP 0.70 and LCP 0.77. It was isolated and sequenced according to Sanger, F. et al., Proc. Natl. Acad. Sci., 74, p. 5463 (1977). The DNA molecules of the 90 bp fragments from both LCP 0.70 and LCP 0.77 corresponded exactly to the carrier protein subunit, S-15, amino acid sequence spanning Gln[23] through Glu[50], as shown below. The top line represents the first 57 amino acids of the carrier protein subunit, S-15, and the bottom line represents the translation of the 84 bp HaeIII fragments. The one non-match is the result of the fact that the amino acid at position 45 was unidentified. DNA molecule analysis identified it as a threonine (T).

```
GASSAGLGPVVRCEPCDARALAQCAPPPAVCAELVREPGCGCCLXCALSEGQPXGIY
                      :::::::::::::::::::::::::  :::::
                      QCAPPPAVCAELVREPGCGCCLTCALSE
```

These clones were designated as cLCP 0.70 and cLCP 0.77, their recombinant DNA molecules as λ gt10:LCP 0.70 and λ gt10:LCP 0.77, and their DNA inserts LCP 0.70 and LCP 0.77. This nomenclature indicates that the clone and recombinant DNA molecule comprises phage λ gt10, containing carrier protein related cDNA isolated from liver cDNA.

Inserts LCP 0.70 and LCP 0.77 were shown to be similar in size and restriction sites. Inserts LCP 0.70 and LCP 0.77 are approximately 700 and 770 bp, respectively. The restriction maps of LCP 0.70 and LCP 0.77 are shown in FIG. 3a. The DNA sequences of the LCP 0.70 and LCP 0.77 inserts, obtained by both single and double-stranded dideoxy-sequencing (Sanger, F., et al., Proc Natl Acad Sci USA 74, 5463 (1977)), are included in the sequence shown in FIG. 4, nucleotides 1-699 and 7-769, respectively. In addition to the amino terminus, tryptic fragments T1' and T10 corresponded to the DNA molecules of these clones. LCP 0.70 and LCP 0.77 are sufficiently large to encode 17,558 and 20,320 dalton proteins, respectively. Thus, the information required to encode the entire S-15 molecule is contained within these inserts.

Identification Of Clones Containing DNA Sequences Coding For Carrier Protein By Cross-Hybridizing To Either LCP 0.70 and LCP 0.77

The recombinant DNA molecules and DNA inserts of clones cLCP 0.70 and cLCP 0.77 isolated as described above, were used to screen the library of clones previously prepared from cDNA by hybridization to phage plaques. This method allows rapid identification of related clones by hybridization of a radioactive probe made from LCP 0.70 to the DNA of recombinant phage fixed on nitrocellulose filters.

Nitrocellulose filters containing phage DNAs that corresponded to phage plaques transferred from LB plates were prepared as described above.

Either the 700 bp LCP 0.70 or the 770 bp LCP 0.77 EcoRI restriction fragment was used to screen human liver random-primed cDNA library H14, human liver oligo-dT-primed cDNA library H10/H14, and human embryonic fibroblast oligo-dT-primed cDNA library WI38. These probes could also be used to screen other cDNA libraries constructed using RNAs from other tissues encoding the carrier protein. In addition they could be used to screen genomic libraries.

The probe fragment (LCP 0.70 or LCP 0.77) was purified by electrophoresis of the EcoRI digestion products of the recombinant DNA molecules (to separate the insert from the cloning vehicle) in about a 1% agarose gel followed by electroelution onto DE81 paper. The specific fragment was then concentrated and $^{32}$P-labelled by "nick translation" by standard procedures.

Hybridization of the above probe to the nitro-cellulose filter containing the cDNA clones was carried out essentially as described above.

About 500,000 clones originating from oligo-dT-primed human liver cDNA library H10/H14 and about 500,000 clones originating from oligo-dT-primed human embryonic fibroblast cDNA library WI38 were screened.

The frequency of positive signals in the WI38 fibroblast library was approximately 0.1%, whereas the frequency in the liver libraries was only 0.01–0.02%. Positive clones were plaque-purified and characterized by restriction mapping and sequence analysis to identify other clones containing carrier protein cDNA. Clones were sequenced using single- and double-stranded sequencing techniques (Sanger).

A clone containing a 2.3 kb insert (cLCP 2.3) was isolated from human liver oligo-dT-primed cDNA library H10/H14 which contains that full-length carrier protein-like coding sequence. Clones containing inserts of 1.8 kb (cFCP 1.8) and 2.5 kb (cFCP 2.5), respectively were isolated from the WI38 fibroblast oligo-dT-primed cDNA library. DNA sequence analysis of the clones (FIG. 4) showed that both contain the entire carrier protein-like polypeptide coding sequence. The encoded protein consists of a 27 amino acid (81 nucleotide) leader plus a 264 amino acid (792 nucleotide) mature coding region. Both the liver and fibroblast clones display essentially the same nucleotide sequence in the coding region. One of the liver clones encodes a GLY instead of an ALA at amino acid position 5, where position 1 is the first amino acid of the mature protein. This polymorphism corresponds to that observed in carrier protein subunits purified from Cohn fraction IV-1.

Figure 3B:
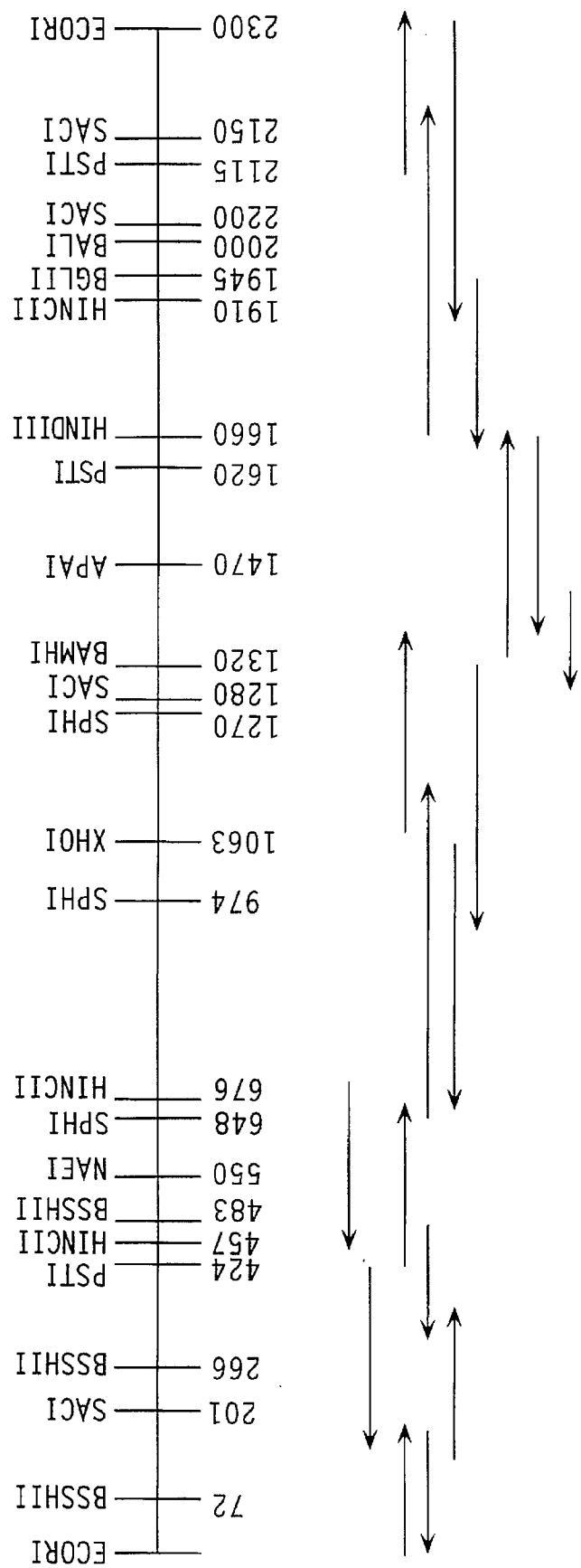
FIG. 3b displays the strategy for sequencing LCP 2.3.

Northern analysis of WI38 human embryonic fibroblast RNA, human liver RNAs H10/H14, human placenta RNA, and macaque liver RNA using LCP 0.70 or LCP 0.77 as a probe indicated that the carrier protein mRNA is approximately 2,000–2,500 bases in size. Thus, the 2.2–2.4 kb clones likely represent full-length cDNAs corresponding to those RNAs. Analysis of the human liver cDNA library and clone cLCP 2.3 by polymerase chain reaction (PCR) amplification (Saiki, R. K., et al. Science 239, pp. 487–491 [1988]) suggests that cLCP 2.3 may have a small deletion of approximately 200 bp in the 3' untranslated region. In fact, recently a clone containing a 2.5 kb insert (cLCP 2.5) was isolated from the liver cDNA library. This insert (LCP 2.5) is the same as LCP 2.3 except for a 200-bp "insertion" between the XhoI site at 1063 and the SphI site at 1270 (FIG. 3b). LCP 2.5 is apparently analogous to FCP 2.5.

It is, of course, evident that this method of clone screening using the DNA insert of clones LCP 0.70 and LCP 0.77, as described above, may be employed equally well on other clones containing DNA molecules arising from recombinant DNA technology, synthesis, natural sources or a combination thereof and on clones containing DNA molecules related to any of the above DNA molecules by mutation, including single or multiple, base substitutions, insertions, inversions, or deletions. Therefore, such DNA molecules and their identification also fall within this invention. It is also to be understood that DNA molecules, which are not screened by the above DNA molecule, yet which as a result of their arrangement of nucleotides code for the polypeptides coded for by the above DNA molecules also fall within this invention.

In addition, because of the expected homology, between the DNA molecule coding for human carrier protein-like polypeptide and the DNA molecule coding for carrier proteins from non-human sources, the DNA molecules of this invention are useful in the selection of the DNA coding for those non-human carrier proteins and in the cloning and expression of those non-human carrier proteins for use in therapeutic compositions and methods. Finally, the DNA molecules of this invention or oligo-nucleotides prepared and derived from them may be employed to select other DNA molecules that encode carrier protein-like polypeptides that may not be the carrier protein or a carrier protein subunit. Those molecules and polypeptides are also part of this invention.

Expression Of Polypeptides Displaying An Activity Of The Carrier Protein

Production of polypeptides by expressing DNA molecules encoding a carrier protein-like polypeptide was carried out in E. coli and mammalian cells.

Expression in E. coli of Full-Length Carrier Protein-Like Sequence With Alternate Signal Sequence A DNA fragment containing the entire coding region of the carrier protein gene in which the gene's signal sequence was replaced by that for preproinsulin was ligated into the expression vector pKK233-2 (Pharmacia). This vector contains a trp-lac fusion promoter in which the −35 trp signal is placed 17 bases (the consensus distance) from the lac −10 region. The presence of the lac operator sequences allows expression from this promoter to be induced by adding IPTG (isopropyl-β-D-thiogalactopyranoside) to the medium. In addition, this vector contains the lacZ ribosome binding site.

Figure 5:
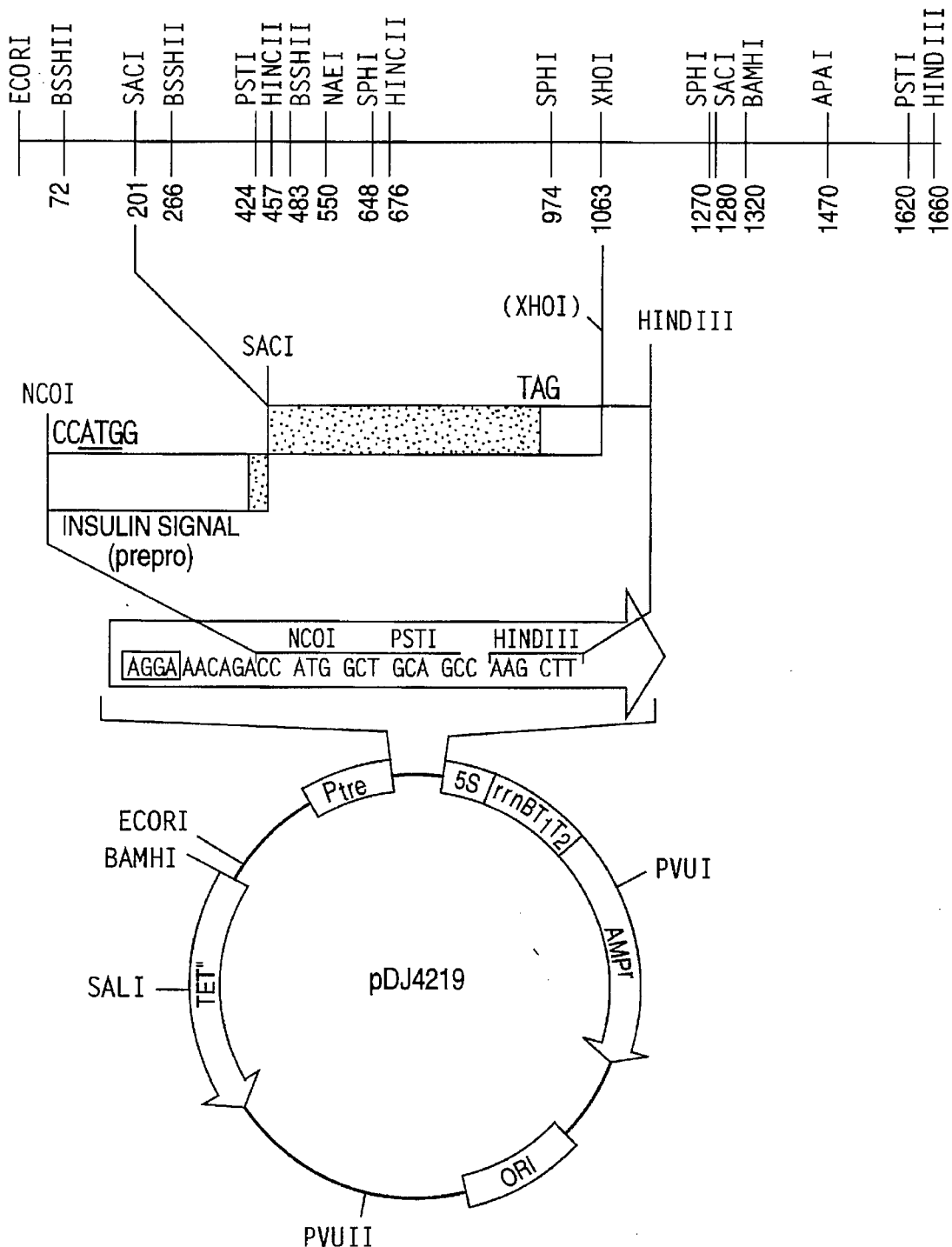
FIG. 5 displays the functional and partial restriction map of vector pDJ4219 which contains a gene for a human carrier protein-like polypeptide having 264 amino acids inserted into pKK233-2, for expression in E. coli cells.

The insert (pDJ4219) containing the preproinsulin signal sequence fused to the carrier protein gene's mature coding sequence was accomplished in the following manner (shown in FIG. 5). A preproinsulin signal sequence was synthesized in which the initiating ATG was contained within an NcoI restriction site. The signal sequence was followed by the nucleotides GGCGCGAGCTCG encoding the first four amino acids of the mature carrier protein, through the SacI site. Thus, it was possible to generate the NcoI/SacI fragment shown in FIG. 5. This fragment was ligated to the SacI/XhoI fragment containing the rest of the coding sequence for the carrier protein, also shown in FIG. 5. The XhoI site, which is located 85 bp beyond the translation termination site, had been converted to a HindIII site by the addition of HindIII linkers using standard procedures. The resulting NcoI/HindIII fragment containing the preproinsulin signal sequence and the carrier protein coding region was inserted into the NcoI and HindIII sites of pKK233-2. Expression of this construction in E. coli induced by IPTG yielded a 25,000–30,000 dalton protein, identified by its ability to bind anti-carrier protein antibody. Expression was carried out in the presence of $^{35}$S-cysteine. Two hours after induction by IPTG, the cell extract (cytoplasm and periplasmic space) was immunoprecipitated with anti-carrier protein antibody and submitted to SDS-PAGE. The ability of the carrier protein to be induced by IPTG was demonstrated, since cells containing this construction grown in the absence of IPTG induction expressed only very small quantities of the 25,000–30,000 dalton protein. Controls in which pKK233-2 alone was tested showed no protein in this size range.

Expression In COS Cells Of A Partial Carrier Protein-Like Sequence

Figure 6:
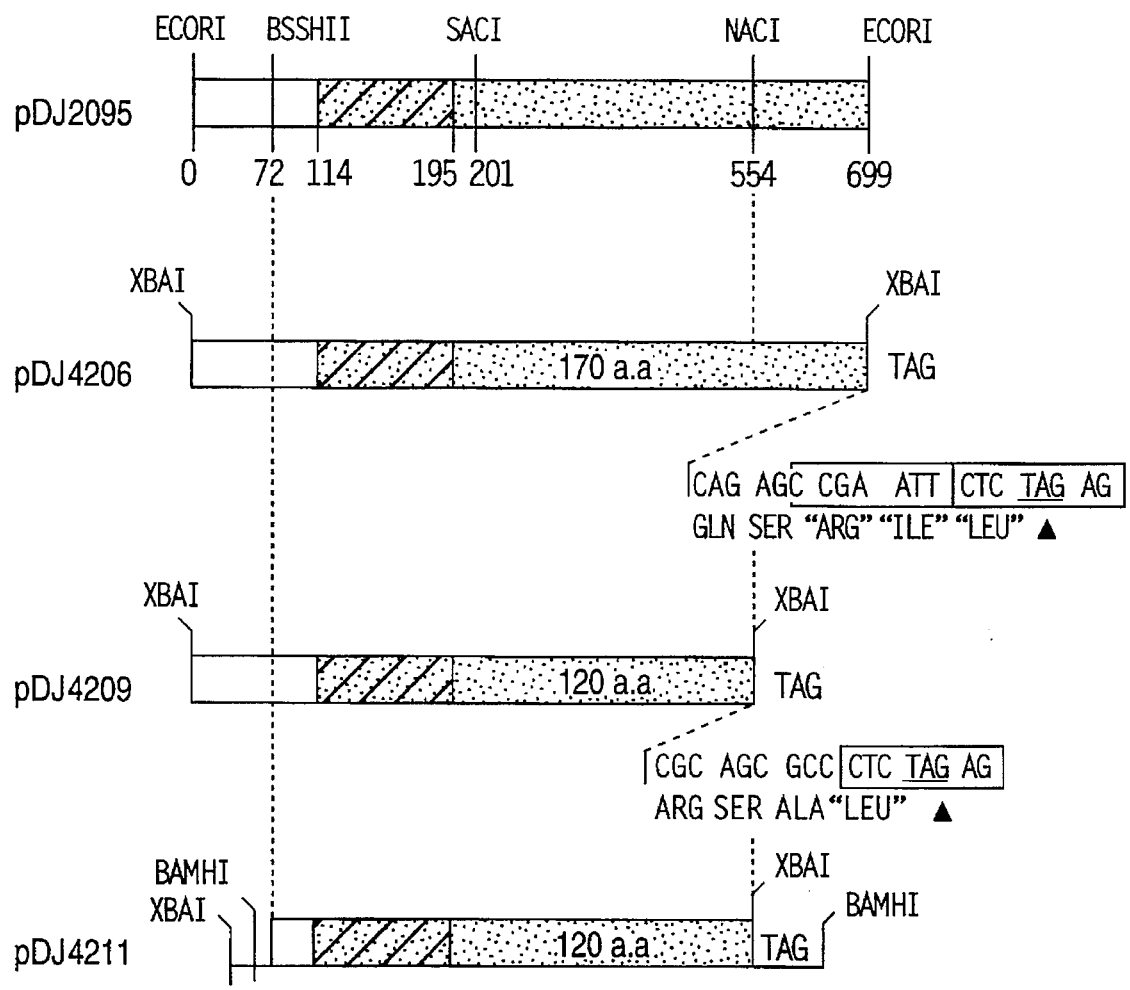
FIG. 6 displays the preparation of various recombinant DNA molecules that may be employed in vectors for transforming appropriate hosts, which when cultured produce carrier protein-like polypeptides.

Insert fragments from pDJ4209 and pDJ4211 (shown in FIG. 6) were ligated into mammalian expression vector pSVL or pDJ4210 (Pharmacia) at the unique XbaI site. pSVL contains the SV40 late promoter, intron, and polyadenylation site. It also has SV40 and pBR322 origins of replication. pDJ4210 is similar to pSVL but contains the origin of replication from pUC19 instead of pBR322.

Figure 7:
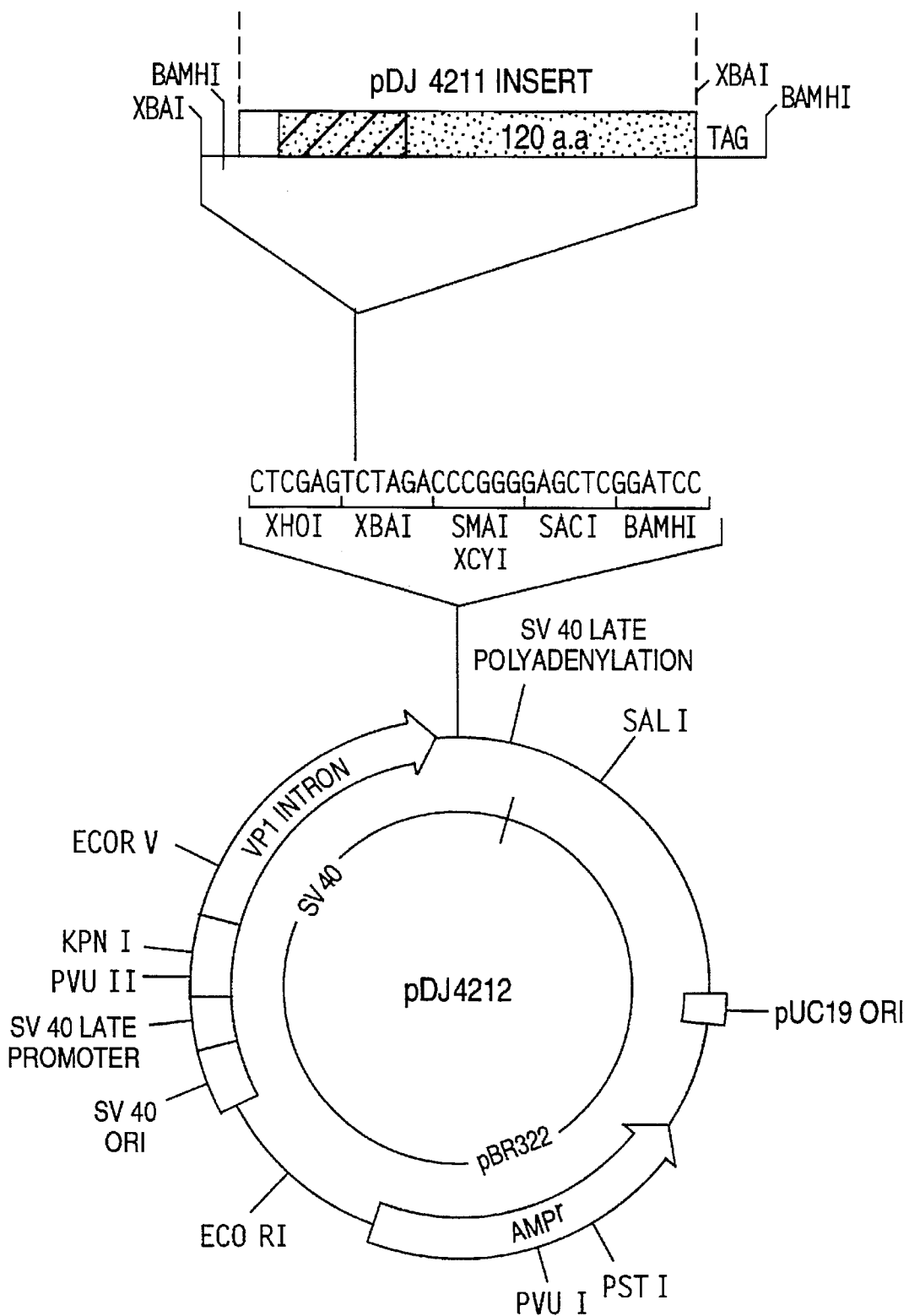
FIG. 7 displays the functional and partial restriction map of vector pDJ4212 which contains a gene for m human carrier protein-like polypeptide having the first 120 amino acids of mature carrier protein that has been inserted into pSVL derivative pDJ4210, for expression in COS cells.

Each of these inserts contains a partial carrier protein gene, specifically the first 120 codons of the mature sequence followed by a synthetic sequence (5'-CTCTAGAG . . . 3') which terminates the reading frame. Each has a different control region:

pDJ4209 contains the entire 5' untranslated region (114 nucleotides) stretching from the EcoRI site, which has been converted to an XbaI site. It also contains the carrier protein signal sequence. The pDJ4209 XbaI fragment contained in pSVL is called pDJ4207.

pDJ4211 contains a 44 nucleotide 5' untranslated region and the carrier protein signal sequence. The pDJ4211XbaI fragment contained in pDJ4210 is called pDJ4212 and is shown in FIG. 7.

The vectors containing the partial carrier protein genes were transfected into COS cells (defective SV40 transformed simian cells) to measure transient expression. Cells were grown in DMEM-F12. Proteins were labelled with $^{35}$S-cysteine. Media was collected, immunoprecipitated with anti-carrier protein antibody, and submitted to SDS-PAGE. Expression studies using pDJ4212 and pDJ4207 yielded two proteins of approximately 14,000 and 16,000 daltons. Expression of these proteins was greater with pDJ4212 than with pDJ4207.

Expression In CHO Cells Of A Full-Length Carrier Protein-Like Sequence

Figure 8:
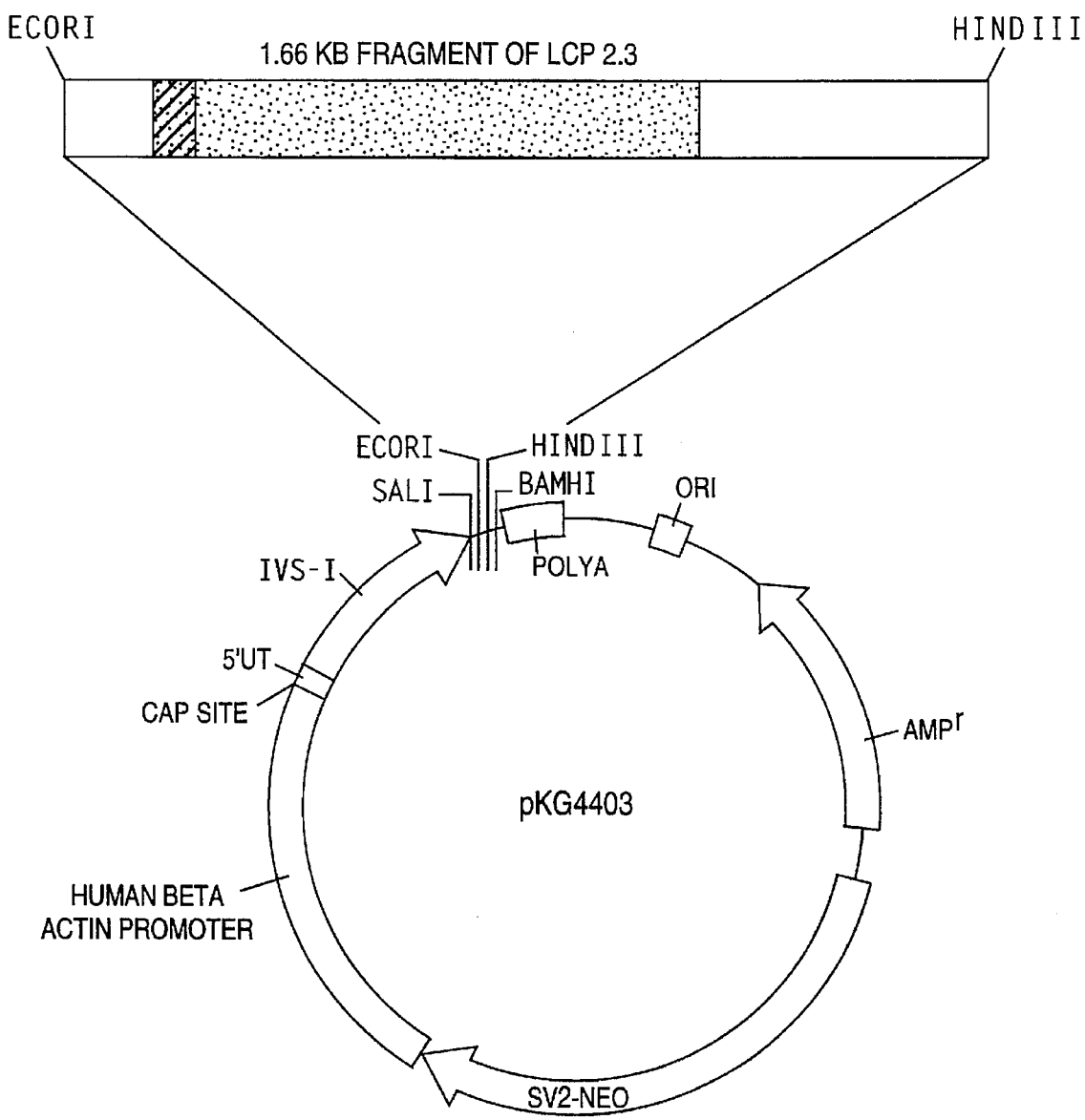
FIG. 8 displays the functional and partial restriction map of vector pKG4403 which contains a gene for a human carrier protein-like polypeptide having 264 amino acids inserted into pKG3226, for expression in CHO cells.

The 1.66 kb EcoRI/HindIII fragment of LCP 2.3 which contains the entire carrier protein gene plus 5' and 3' untranslated regions (114 and 700 nucleotides, respectively) was inserted into mammalian expression vector pKG3226 which contains a β-actin promoter (licensed from Stanford University) and other functions necessary for expression in mammalian cells. The resultant vector, called pKG4403 is shown in FIG. 8. pKG4403 was transformed into CHO (Chinese hamster ovary) cells; stably transformed lines were established by drug selection. Serum-free conditioned media from the transformed CHO pool was analyzed for carrier protein-like polypeptide expression by immunoprecipitation of $^{35}$S-labelled products and by ability to bind $^{125}$I-SM-C in an SM-C Western. For detection by immunoprecipitation, cells were grown to 80% confluence in DMEM-F12 supplemented with 10% fetal bovine serum, switched to serum-free media starved for cysteine 1 hour, and subsequently labelled overnight with $^{35}$S-cysteine. The media was immunoprecipitated with anti-carrier protein subunit antibody, and the resulting proteins were analyzed by SDS-PAGE under reducing conditions. Carrier protein-like polypeptides of 37,000 and 39,000 daltons were specifically identified. For detection by SM-C binding, serum-free conditioned media (unlabelled) was collected 48 hours after seeding the transformed pool and was subjected to SDS-PAGE under nonreducing conditions. The proteins were transferred from the gel to a nitrocellulose filter which was probed with $^{125}$I-SM-C. Two novel carrier protein-like polypeptides of 43,000 and 45,000 daltons were observed. A 23,000 dalton protein endogenous to CHO cells was detected in the transformed pool as well as in the non-transformed control CHO pool. The size difference (37,000 and 39,000 versus 43,000 and 45,000) is likely due to whether SDS-PAGE was conducted under reducing or non-reducing conditions.

This gene of LCP 2.3 does not exclude the possibility that modifications to the gene such as mutations, including single or multiple, base substitutions, deletions, insertions, or inversions may not have already occurred in the gene or may not be employed subsequently to modify its properties or the properties of the polypeptides expressed therefrom. Nor does it exclude any polymorphism which may result in physiologically similar but structurally slightly different genes or polypeptides than that shown in FIG. 4.

It should, of course, be understood that cloned cDNA from polyA$^+$ RNA by the usual procedures may lack 5'-terminal nucleotides and may even contain artifactual molecules.

The structure of the polypeptide depicted in FIG. 4, of course, does not take into account any modifications to the polypeptide caused by its interaction with in vivo enzymes, e.g., glycosylation. Therefore, it must be understood that the amino acid molecule depicted in FIG. 4 may not be identical with carrier protein produced in vivo.

It should be understood that while the chromosomal gene encoding carrier protein activity may not be expressible in bacterial hosts because these intervening molecules may not be processed correctly by such hosts, the chromosomal genes are likely to be very useful in the production of carrier protein-like polypeptides in eukaryotic hosts where the human noncoding regions, introns and coding regions may be important for high levels of expression and correct processing of the product to biologically active carrier protein-like polypeptides.

Improving The Yield And Activity Of Polypeptides Displaying Carrier Protein Activity The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide molecules, normally situated ahead of the desired coding molecule. These nucleotide molecules or expression control molecules define the location at which RNA polymerase interacts to initiate transcription (the promoter molecule ) and at which ribosomes bind and interact with the mRNA (the product of transcription) to initiate translation. Not all such expression control molecules function with equal efficiency. It is thus of advantage to separate the specific coding molecules for the desired protein from their adjacent nucleotide molecules and to fuse them instead to other known expression control molecules so as to favor higher levels of expression. This having been achieved, the newly engineered DNA fragments may be inserted into higher copy number plasmids or bacteriophage derivatives in order to increase the number of gene copies within the cell and thereby further to improve the yield of expressed protein.

Several expression control molecules may by employed as described above. These include the operator, promoter and ribosome binding and interaction molecules (including molecules such as the Shine-Dalgarno molecules) of the lactose operon of E. coli ("the lac system"), the corresponding molecules of the tryptophan synthetase system of E. coli ("the trp system"), the major operator and promoter regions of phage λ ($O_L P_L$ and $O_R P_R$), the bacteriophage T7 promoter recognized only be T7 RNA polymerase, a control region of Filamenteous single-stranded DNA phages, SV40 early and late promoters, actin promoters, promoters located on the long terminal repeats of retroviruses, or other molecules which control the expression of genes of prokaryotic or eukaryotic cells and their viruses or combinations thereof. Therefore, to improve the production of a particular polypeptide in an appropriate host, the gene coding for that polypeptide may be prepared as before and inserted into a recombinant DNA molecule closer to its former expression control molecule or under the control of one of the above improved expression control molecules. Such methods are known in the art.

Other methods to improve the efficiency of translation involve insertion of chemically or enzymatically prepared oligonucleotides in front of the initiating codon. By this procedure a more optimal primary and secondary structure of the messenger RNA can be obtained. More specifically, a molecule can be so designed that the initiating AUG codon occurs in a readily accessible position (i.e., not masked by secondary structure) either at the top of a hairpin or in other single-stranded regions. Also the position and molecule of the aforementioned Shine-Dalgarno segment can likewise be optimized. The importance of the general structure (folding) of the messenger RNA has been documented.

Further increases in the cellular yield of the desired products depend upon an increase in the number of genes that can be utilized in the cell. This may be achieved by insertion of the carrier protein-like gene (with or without its transcription and translation control elements) in a higher copy number plasmid or in a temperature-controlled copy number plasmid (i.e., a plasmid which carries a mutation such that the copy number of the plasmid increases after shifting up the temperature.

Alternatively, an increase in gene dosage can be achieved for example by insertion of recombinant DNA molecules engineered in the way described previously into the temperate bacteriophage, most simply by digestion of the plasmid with a restriction enzyme, to give a linear molecule which is then mimed with a restricted phage λ cloning vehicle and the recombinant DNA molecule produced by incubation with DNA ligase. The desired recombinant phage is then selected as before and used to lysogenize a host strain of E. coli.

Therefore, it should be understood that the insert DNA of this invention may be inserted into other expression vectors, as previously described (supra) and these vectors employed in various hosts, as previously described (supra) to improve the expression of the gene coding for carrier protein subunit.

The biological activity of the carrier protein-like polypeptides produced in accordance with this invention may also be improved by using the DNA molecules of this invention to transform mammalian cell systems and to express the gene in those systems. Such mammalian systems are known. One such system is the CHO (Chinese Hamster ovary) (DHFR⁻) cell system in which the gene expression may be amplified by methotrexate (MTX). These expression systems permit the production of glycosylated proteins. Such cells can be induced to greatly amplify the copy number of the carrier protein-like gene.

It should also be understood that carrier protein-like polypeptides may also be prepared in the form of a fused protein (e.g., linked to a prokaryotic or eukaryotic N-terminal segment directing excretion), in the form of procarrier protein-like polypeptide (e.g., starting with all or parts of the carrier protein signal molecule which could be cleaved off upon excretion) or as a mature carrier protein-like polypeptide (by cleavage of any extraneous amino acids, including an initial methionine during expression and excretion) or in the form of a f-met-carrier protein-like polypeptide. One particularly useful polypeptide in accordance with this invention would be mature carrier-like polypeptide with an easily cleaved amino acid or series of amino acids attached to the amino terminus. Such constructions would allow synthesis of the protein in an appropriate host, where a start signal not present in mature carrier protein subunits is needed, and then cleavage of the extra amino acids to produce mature carrier protein subunits.

When the carrier protein subunit or carrier protein-like polypeptide is to be used in combination with somatomedin-like molecules for therapy, the two molecules could be co-produced in the same cell, preferably in mammalian cells. Vectors containing both genes could be cotransformed and stable cell lines selected that expressed both proteins. Thus, only one fermentation and purification scheme would be required to produce the complex containing both carrier protein-like and the somatomedin-like polypeptides.

The yield of these different forms of polypeptide may be improved by any or a combination of the procedures discussed above. Also different codons for some or all of the codons used in the present DNA molecules could be substituted. These substituted codons may code for amino acids identical to those coded for by the codons replaced but result in higher yield of the polypeptide. Alternatively, the replacement of one or a combination of codons leading to amino acid replacement or to a longer or shorter carrier protein-like polypeptide may alter its properties in a useful way (e.g., increase the stability, increase the solubility, increase the therapeutic activity).

Finally, the activity of the polypeptides produced by the recombinant DNA molecules of this invention may be improved by fragmenting, modifying or derivatizing the DNA molecules or polypeptides of this invention by well-known means, without departing from the scope of this invention.

While, we have described certain embodiments of the invention, it is apparent that those embodiments can be altered to provide other embodiments which utilize the processes and compositions of the invention. The scope of the invention is defined by the following claims rather than by the specific embodiments that have been presented by way of example.

What is claimed is:

1. A method for measuring the level of unbound somatomedins in human fluids comprising:

contacting an antibody with said human fluids which binds specifically to a carrier protein subunit which:
(a) has the N-terminal amino acid sequence, Gly-Ala-Ser-Ser-Ala-Gly-Leu-Gly-Pro-Val-Val-Arg-R-Glu-Pro-R-Asp-Ala-Arg-Ala-Leu-Ala, wherein R is a cysteine or half-cysteine;
(b) binds insulin-like growth factor 1 (IGF-I); and
(c) has a molecular weight of about 15,000 to 30,000 daltons as determined by sodium dodecyl sulfate gel electrophoresis under reducing conditions to separate somatomedins complexed with carrier protein subunits having the N-terminal amino acid sequence Gly-Ala-Ser-Ser-Ala-Gly-Leu-Gly-Pro-Val-Val-Arg-R-Glu-Pro-R-Asp-Ala-Arg-Ala-Leu-Ala- from the somatomedins not bound to said carrier protein subunits, and measuring said somatomedins not bound to said carrier protein subunits.

2. The method of claim 1 wherein said somatomedins not bound to said carrier protein subunits are measured by RIA.

* * * * *

UNITED STATES PATENT AND TRADEMARK OFFICE
CERTIFICATE OF CORRECTION

PATENT NO.     : 5,624,805
DATED          : April 29, 1997
INVENTOR(S)    : Spencer et al.

It is certified that error appears in the above-identified patent and that said Letters Patent is hereby corrected as shown below:

The drawing sheet consisting of figure 4B should be deleted, and replaced with the drawing sheet consisting of figure 4B, as shown on the attached sheet.

The drawing sheet consisting for figure 4c should be added as shown on the attached sheet and renumbered as sheet 7 of 12.

Drawing sheets to be renumbered as 1 of 12 – 12 of 12

Signed and Sealed this

Twenty-ninth Day of April, 2003

JAMES E. ROGAN
*Director of the United States Patent and Trademark Office*

```
                                                          (486)
     GGC CGC GGG CTC TGC GTC AAC GCT AGT GCC GTC AGC CGC CTG CGC
      G   R   G   L   C   V   N   A   S   A   V   S   R   L   R
         (110)                                 (120)

(531)
 5   GCC TAC CTG CTG CCA GCG CCG CCA GCT CCA GGA AAT GCT AGT GAG
      A   Y   L   L   P   A   P   P   A   P   G   N   A   S   E
                             (130)

(576)
     TCG GAG GAA GAC CGC AGC GCC GGC AGT GTG GAG AGC CCG TCC GTC
      S   E   D   R   S   A   G   S   V   E   S   P   S   V
10      (140)                                  (150)

(621)
     TCC AGC ACG CAC CGG GTG TCT GAT CCC AAG TTC CAC CCC CTC CAT
      S   S   T   H   R   V   S   D   P   K   F   H   P   L   H
                             (160)

(666)
15   TCA AAG ATA ATC ATC ATC AAG AAA GGG CAT GCT AAA GAC AGC CAG
      S   K   I   I   I   I   K   K   G   H   A   K   D   S   Q
         (170)                                 (180)

(711)
     CGC TAC AAA GTT GAC TAC GAG TCT CAG AGC ACA GAT ACC CAG AAC
      R   Y   K   V   D   Y   E   S   Q   S   T   D   T   Q   N
20                           (190)

(756)
     TTC TCC TCC GAG TCC AAG CGG GAG ACA GAA TAT GGT CCC TGC CGT
      F   S   S   E   S   K   R   E   T   E   Y   G   P   C   R
         (200)                                 (210)

(801)
25   AGA GAA ATG GAA GAC ACA CTG AAT CAC CTG AAG TTC CTC AAT GTG
      R   E   M   E   D   T   L   N   H   L   K   F   L   N   V
                             (220)

(846)
     CTG AGT CCC AGG GGT GTA CAC ATT CCC AAC TGT GAC AAG AAG GGA
      L   S   P   R   G   V   H   I   P   N   C   D   K   K   G
30      (230)                                  (240)

(891)
     TTT TAT AAG AAA AAG CAG TGT CGC CCT TCC AAA GGC AGG AAG CGG
      F   Y   K   K   K   Q   C   R   P   S   K   G   R   K   R
                             (250)

35                        FIG. 4B
```

```
                                                              (930)
  GGC TTC TGC TGG TGT GTG GAT AAG TAT GGG CAG CCT CTC CCA GGC
   G   F   C   W   C   V   D   K   Y   G   Q   P   L   P   G
     (260)                                 (270)

(981)
5 TAC ACC ACC AAG GGG AAG GAG GAC GTG CAC TGC TAC AGC ATG CAG
   Y   T   T   K   G   K   E   D   V   H   C   Y   S   M   Q
                         (280)

AGC AAG TAG
   S   K   *
     (290)
```

FIG. 4C